United States Patent [19]

Ross et al.

[11] Patent Number: 4,795,748
[45] Date of Patent: Jan. 3, 1989

[54] ANTIBACTERIAL 7-OXO-4-THIA-1-AZABICYCLO[3,2,0]HEPT-2-ENE DERIVATIVES

[75] Inventors: Barry C. Ross, Luton; Michael D. Cooke, Newport Pagnell; Nicholas I. Carruthers; Andrew J. Barker, both of Milton Keynes, all of Great Britain

[73] Assignee: Hoechst UK Limited, Hounslow, Great Britain

[21] Appl. No.: 749,384

[22] Filed: Jun. 27, 1985

[30] Foreign Application Priority Data

Jun. 29, 1984 [GB] United Kingdom ............... 8416565

[51] Int. Cl.$^4$ .................. C07D 499/00; A61K 31/425
[52] U.S. Cl. .................................. 514/192; 514/195; 540/310
[58] Field of Search ............... 540/310, 350; 514/195, 514/192

[56] References Cited

U.S. PATENT DOCUMENTS 4,585,767 4/1986 Cooke et al. ............ 514/210
4,738,959 4/1988 Cooke et al.

FOREIGN PATENT DOCUMENTS 0002210 6/1979 European Pat. Off.
0069377 1/1983 European Pat. Off.
2042515 9/1980 United Kingdom.
2104511 3/1983 United Kingdom.
2122619A 1/1984 United Kingdom.

Primary Examiner—Nicholas S. Rizzo
Attorney, Agent, or Firm—Finnegan, Henderson, Farabow, Garrett, & Dunner

[57] ABSTRACT

A compound of the formula I

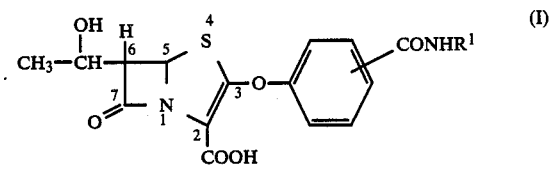

in which $R^1$ represents a hydrogen atom or an alkyl group having from 1 to 4 carbon atoms, the —CONHR$^1$ group being present at the 3- or 4-position on the phenyl ring, and esters thereof at the 2-carboxyl group and/or at the 8-hydroxy group, have antibacterial and/or β-lactamase inhibiting activity.

26 Claims, No Drawings

ANTIBACTERIAL 7-OXO-4-THIA-1-AZABICYCLO[3,2,0]HEPT-2-ENE DERIVATIVES

This invention relates to penem derivatives, to a process for their preparation, to pharmaceutical preparations comprising them, and to intermediates for use in the preparation of substances having antibacterial activity and/or β-lactamase inhibitory and/or inactivating activity.

7-Oxo-4-thia-1-azabicyclo[3,2,0]hept-2-ene has the following formula A, and derivatives thereof having an aliphatic side chain at position 6 are numbered as shown in formula B:

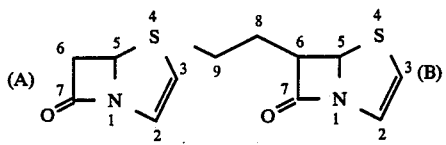

By an alternative system of nomenclature, the above nucleus A may be described as a "penem", in which case the ring numbering is as shown in formula C, with derivatives having an aliphatic side chain at position 6 being numbered as shown in formula D:

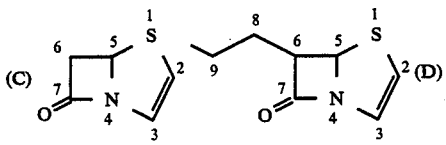

The present invention provides a compound of formula I

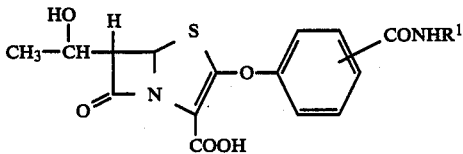

in which $R^1$ represents a hydrogen atom or an alkyl group having from 1 to 4 carbon atoms, for example, a methyl, ethyl, n-propyl, iso-propyl, n-butyl, iso-butyl, sec-butyl or t-butyl group, the —CONHR$^1$ group being present at the 3- or 4-position on the phenyl ring.

$R^1$ preferably represents a hydrogen atom.

The present invention also provides esters of a compound of formula I at the 2-carboxyl group, for example, esters that can be converted by hydrolysis, by photolysis, by reduction or, especially, by esterase enzyme action, to give the free acid of formula I. The present invention further provides esters at the 8-hydroxy group, especially lower alkanoyloxy groups at the 8-position.

The present invention further provides salts of a compound of formula I, especially physiologically tolerable salts thereof.

The stereochemistry at positons 5, 6 and 8 of a compound of formula I can be R or S, independently (R and S being as defined by the Cahn-Ingold-Prelog system of nomenclature). The preferred stereochemistry at position 5 is R, at position 6 is S, and at position 8 is R.

The present invention also provides a process for the production of a compound of the general formula I, or an ester or salt thereof, which comprises reacting a compound of formula II or of formula IX

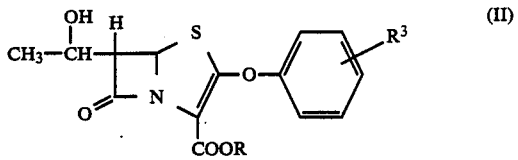

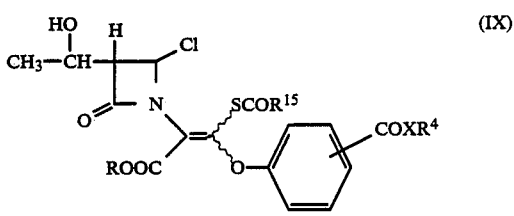

in which R represents a hydrogen atom or a carboxy protecting group, $R^3$ represents an activated carboxylic acid group, $R^4$ represents an alkyl group having from 1 to 4 carbon atoms, or a phenyl group which may be unsubstituted or substituted by one or more substituents, which may be the same or different, selected from chlorine and fluorine atoms, cyano and nitro groups, and alkoyy groups, $R^{15}$ represents a phenyl group or an alkyl group having from 1 to 4 carbon atoms, and X represents an oxygen or sulphur atom, with an amine of formula III $$R^1NH_2 \quad \text{(III)}$$

in which $R^1$ is as defined above to give a compound of formula I or an ester thereof of formula Ia

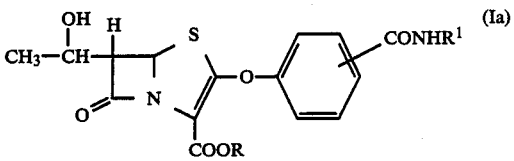

in which $R_x$ represents a carboxy protecting group and, if desired, carrying out any one or more of the following steps in any desired order:

(a) hydrolysing an ester of formula Ia to give the corresponding free acid of formula I,
(b) reacting a free acid of formula I or a salt thereof with an agent capable of forming an ester, for example, with an alcohol, a phenol or a reactive derivative thereof to give an ester of formula Ia,
(c) carrying out an acid or base catalysed ester interchange on an ester of formula Ia to give a different ester of formula Ia,
(d) reacting a free acid of formula I with a base to give a salt at the carboxylic acid group at position 2,
(e) reacting a free acid of formula I or an ester of formula Ia having a basic group with an acid to give an acid addition salt thereof,
(f) hydrolysing the ester group from an ester of formula Ia in the presence of a salt-forming agent, for example, an alkali metal salt, to give a salt of a compound of formula I,
(g) reacting a salt of a compound of formula I with an acid to give a free acid of formula I, and (h) reacting a compound of formula I or a salt thereof, or an ester of formula Ia, with an organic acid to give a compound of formula I or an ester of formula Ia having an esterified hydroxy group at the 8-position.

In a particularly preferred case, the activated carboxylic acid group $R^3$ in compound II is a group of formula —$COXR^4$ in which X and $R^4$ are as defined above, giving a compound of formula IV

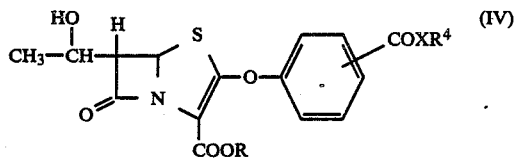

In a compound of formula IV or formula IX, $R^4$ preferably represents a phenyl group substituted by one or more chlorine and/or fluorine atoms. When X represents a sulphur or oxygen atom, $R^4$ especially represents a pentafluorophenyl group, and when X represents a sulphur atom, 4-chlorophenyl and 2,4,5-trichlorophenyl groups are also particularly preferred as $R^4$.

Reaction of the compound of formula IV with the amino compound of formula III is preferably carried out at a temperature within the range of from $-40°$ to $+40°$ C., preferably from $0°$ to $20°$ C. The choice of solvent is wide, provided that the solvent does not itsllf react with any of the reagents or intermediates. For this reason it is often preferable to use a solvent or solvent mixture that is substantially free of water. Examples of suitable solvents are dimethylformamide and acetonitrile.

The reaction between an amine of formula III and a compound of formula IV may be carried out in the presence of a metal salt, especially a salt of a metal selected from Groups IB, IIB and VIII of the Periodic Classification of the Elements (cf E. Cartmell & G. W. A. Fowles, Valency and Molecular Structure, Butterworths, 1966), for example, a salt of copper, rhodium, mercury, zinc, cadmium or, especially, silver. The salt is for example, a salt with an organic or inorganic acid, for example, with perchloric, tetrafluoroboric, acetic, trifluoromethanesulphonic, or trifluoroacetic acid, or with imidazole. Examples of preferred salts are silver acetate, silver trifluoroacetate, silver trifluoromethanesulphonate, and silver imidazolide.

The degree of advantage resulting from the presence of a metal salt during the reaction between an amine of formula III and a compound of formula IV depends on the reactivity of the —$COXR^4$ group in the compound of formula IV, and may be determined empirically, for example, there is not generally a substantial advantage when X represents an oxygen atom. In the case of a compound of formula IV having a pentafluorophenythio -(carbonyl) ester group, a metal salt may be used if desired, but the resulting advantage is not large, whereas for other compounds of formula IV in which X represents a sulphur atom, the presence of a metal salt during the reaction with an amine of formula III results in a greatly improved yield.

A compound of formula IX may be reacted with an amine of formula III under conditions analogous to those described above for the reaction between compounds IV and III to give a compound of formula I or an ester thereof directly. In this case, it is generally necessary to use at least two molar equivalents of the amine. In formula IX, $R^4$ especially represents a pentafluorophenyl group.

An advantage of the preferred compounds of formula IV over other compounds of formula II is that the activated carboxylic acid group —$COXR^4$ can be introduced at an early stage in the reaction sequence leading to the production of compound IV and is carried through the reaction sequence as shown in Reaction Scheme I below. The production of the other activated acids of formula II involves an extra activating step as shown in Reaction Scheme II below, as in this case, these compounds must be produced via a free carboxylic acid of formula V

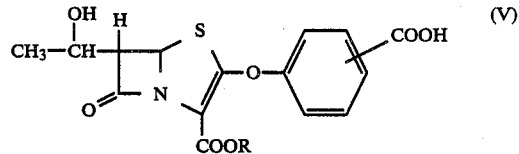

in which R is as defined above.

Overall, a free carboxylic acid group (in compound V) is converted into an amide group (in compound I). The intermediate activated compound of formula II may be produced in a separate reaction step and isolated, if desired, or it may be converted in situ into a compound of formula I.

The conversion of a carboxylic acid group into an amide group is well known in chemistry, and there is available to those versed in the art a wide range of reagents and methods. In general, the reagents function by converting a carboxylic acid group into an activated derivative thereof, which derivative is then reacted with an amine. Examples of the activation of a carboxylic acid group are by conversions as follows:

(i) to an activated ester, for example, to a phenyl ester using, for example, a bisphenyl carbonate;

(ii) to a phosphorous or phosphoric ester, or a phosphoric acid anhydride, using for example, a phosphinyl halide or a phosphoryl halide;

(iii) to a carboxylic acid anhydride, especially a mixed anhydride, using for example, an acid chloride or bromide, for example, pivaloyl bromide, a carbodiimide, for example, dicyclohexylcarbodiimide or 1-(3-dimethylaminopropyl)-3-ethylcarbodiimide, or a chloroforxate;

(iv) to an imidazolide using, for example, N,N'-carbonyldiimidazole;

(v) to an acid chloride using, for example, thionyl chloride; or (vi) to an O-acylurea using, for example, a carbodiimide, for example, as described above, and if desired, converting the O-acylurea into an active ester, for example, an ester with 1-hydroxybenzotriazole or with N-hydroxysuccinimide.

Examples of activated acid groups $R^3$ that can be converted into groups of formula —$CONHR^1$ under reaction conditions that do not affect other parts of the compound of formula II (other than groups —$COXR^4$ as defined above) are, for example, groups of the formula —$COOR^5$ in which $R^5$ represents one of the following groups

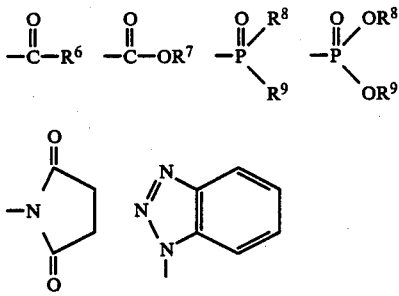

in which R⁶ represents an alkyl group having up to 4 carbon atoms, especially a t-butyl group; R⁷ represents an alkyl group having up to 4 carbon atoms, especially an iso-butyl group; R⁸ and R⁹, which may be the same or different, each represents an alkyl group having up to 4 carbon atoms or a phenyl group.

The above methods are examples of the techniques available in the art, and do not constitute an exhaustive list. For further information see, for example, M. Bodanszky, Y. S. Klausner and M. A. Ondetti, "Peptide Synthesis", J. Wiley and Sons, New York, 1976, and N. F. Norton, Organic Reactions, Vol. 12, 157 (1962).

Some of the methods for converting a carboxylic acid group into an amide are extremely mild and therefore well suited to the conversion of a penem containing a carboxylic acid group into a penem containing an amide group without damage to any other part of the molecule. Thus, for example, a solution of a carboxylic acid of formula V in an inert solvent, for example, dichloromethane, acetonitrile or tetrahydrofuran, may be treated with a carbodiimide, for example, dicyclohexylcarbodiimide and 1-hydroxybenzotrizzole at a temperature within the range of from −40° to +40° C., preferably from 0° to 20° C., to form the benzotriazol-1-yl ester.

An activated penem of formula II formed from a free acid of formula V may be reacted in situ with the amino compound of formula III to form a compound of formula I or an ester thereof, or the activated penem of formula II may first be isolated and purified before reaction with the amino compound. Reaction of the activated penem in either case with the amino compound III is preferably carried out at a temperature within the range of from −40° to +40° C., preferably from 0° to 20° C. The choice of solvent is wide, provided that the solvent does not itself react with any of the reagents or intermediates. For this reason it is often preferable to use a solvent or solvent mixture that is substantially free of water.

The compound of formula I produced from compound II or from compound IV may be converted, if desired, into an ester of formula Ia, and an ester of formula Ia produced from compound II or IV may be converted into the corresponding free acid of formula I, as described above. Other acid/ester/salt interconversions can also be carried out as described above.

As indicated above, a compound of formula I may be in the form of an ester at the carboxy group at postion 2, that is to say, a compound of formula Ia. Such an ester is particularly one that can be converted into the free acid by hydrolysis, photolysis, reduction or esterase enzyme action. Examples of such esters are those formed with unsubstituted or substituted aliphatic alcohols or phenols having up to 20 carbon atoms in total. In an esterified carboxy group of formula —COOR, the group R may be, for example, a straight or branched chain substituted or unsubstituted alkyl, alkenyl or alkynyl group having up to 18 carbon atoms, preferably up to 8 carbon atoms, and especially up to 4 carbon atoms, for example, a methyl, ethyl, n-propyl, iso-propyl, n-butyl, sec-butyl, iso-butyl, tert-butyl, n-pentyl, n-hexyl, allyl or vinyl group. An aliphatic group R, especially a methyl or ethyl group, may be substituted, for example, by an acyloxy group (further details of such groups are given below); by an aminoalkanoyloxy group; by an optionally substituted 2-amino group; or by one or more unsubstituted or substituted phenyl groups. A phenyl group, either as a phenol or as a substituent of an aliphatic group, may be substituted, for example, by one or more substitutents, selected especially from nitro groups and halogen atoms. Examples of phenyl substituted-aliphatic groups, are benzyl, p-nitrobenzyl, benzhydryl and trityl groups.

As indicated above, an ester group is especially one that can be removed by hydrolysis, photolysis, reduction or enzyme action, or two or more of these methods may be used, for example, reduction followed by hydrolysis. A group R that can be removed readily without substantial degradation of the rest of the molecule is particularly useful as a carboxy protecting group. Examples of esters that are readily split by reduction are phenyl substituted-methyl esters, which may be unsubstituted or substituted, for example, benzyl, p-nitrobenzyl, benzhydryl and trityl esters.

Reduction of an ester, for example, a phenyl substituted-methyl ester, for example, a p-nitrobenzyl ester, may be carried out using hydrogen and a metal catalyst, for example, a noble metal catalyst, for example, platinum, palladium or rhodium, which catalyst may be supported, for example, on charcoal or kieselguhr.

Alternatively, a p-nitrobenzyl ester may be converted into the corresponding free acid by a two-step method, with an initial reduction of the nitro group followed by hydrolysis. The nitro group may be reduced by noble metal catalysed hydrogenation, for example, using platinum, or palladium on carbon, or by a metal reducing agent, for example, zinc in acetic acid. Other metal reducing agents are, for example, aluminium amalgam, and iron and ammonium chloride, see for example, British Patent Specification No. 1,582,960. Reduction of the nitro group is followed by hydrolysis which may occur in situ during reduction of the nitro group or which may be carried out subsequently by treatment with an acid or a base.

An o-nitrobenzyl ester may be converted into the corresponding free acid by photolysis.

Certain ester groups may be split off by base hydrolysis, for example, acetylmethyl and acetoxymethyl ester groups.

There may be used an esterifying group that is removable under physiological conditions, that is to say, the esterifying group is split off in vivo to give the free acid or the carboxylate, for example, an acyloxymethyl or acyloxyethyl ester, for example, an acetoxymethyl, 1'-(acetoxy)ethyl or pivaloyloxymethyl ester, a 5-methyldioxalen-2-on-4-yl-methyl ester, an aminoalkanoyloxymethyl ester, for example, a glycyloxymethyl, L-valyloxymethyl or L-leucyloxymethyl ester, or a phthalidyl ester, or a 1'-(alkoxycarbonyloxy)ethyl ester, for example, a 1'-(methoxycarbonyloxy)ethyl ester, or an optionally substituted 2-aminoethyl ester, for example, a 2-diethylaminoethyl or 2-(1-morpholino)-ethyl ester (acyl and alkanoyl groups having 1 to 12 carbon atoms).

Preferred esters are the p-nitrobenzyl, phthalidyl, pivaloyloxymethyl, ethoxycarbonyloxymethyl, 5-methyldioxalen-2-on-4-yl-methyl, acetylmethyl, acetoxymethyl, acetoxyethyl, acetylethyl and ethoxycarbonyloxyethyl esters.

An ester of a compound of formula I, or of any other free acid described herein, may be prepared by reaction of the appropriate free acid with an alcohol, a phenol or a reactive derivative thereof. The reaction is preferably carried out under mild conditions in order to prevent rupture of the ring system, for example under neutral or mild acidic or basic conditions, and at temperatures within the range of from −70° to +35° C.

An ester derived from an alcohol may also be produced by reaction of a reactive derivative of the alcohol, for example, a halide, for example, a chloride, bromide or iodide, or hydrocarbonsulphonyl derivative, for example, a mesyl or tosyl ester, with a salt of an acid of formula I or of another free acid described herein, for example, an alkali or alkaline earth metal salt, for example, a lithium, sodium, potassium, calcium or barium salt, or an amine salt, for example, a triethylammonium salt. The reaction is preferably carried out in a substituted sulphoxide or amide solvent, for example, in dimethyl sulphoxide, dimethylformamide, or hexamethylphosphoramide or, alternatively, an ester may be prepared by reaction of the acid with the alcohol or phenol in the presence of a condensing agent, for example, dicyclohexylcarbodiimide.

The present invention also provides salts of those compounds of formula I that have salt-forming groups, especially the salts of a free acid of formula I and acid addition salts of compounds of formula I having a basic group. The salts are especially physiologically tolerable salts, for example, alkali metal and alkaline earth metal salts, for example, sodium, potassium, lithium, calcium, and magnesium salts, ammonium salts, and salts with organic amines; also physiologically tolerable acid addition salts. These may be formed with a suitable inorganic or organic acid, for example, hydrochloric acid, sulphuric acid, or an organic carboxylic or organic sulphonic acid, for example, p-toluene-sulphonic acid.

A salt of a free acid of formula I may be produced by reacting the free acid with the appropriate base in a solvent, preferably under those conditions under which the salt precipitates. A preferred base is potassium 2-ethyl hexanoate.

A salt may be produced directly from an ester by splitting off the ester group under suitable reaction conditions, for example, catalytic reduction of an ester, for example, a p-nitrobenzyl ester, in an aqueous/organic solvent, for example, comprising water and ethyl acetate, dioxane or tetrahydrofuran, in the presence of a metal salt, especially a metal bicarbonate, for example, in an equivalent amount or in a slight excess, yields the salt directly.

As described above, a compound of formula I may also form an ester at the 8-hydroxy group. Such an ester group is especially one that can be removed in vivo to give the free hydroxy group, that is to say, an ester group that can be removed under physiological conditions. Examples of suitable esterifying groups are those of the formula $R_xCO$, in which $R_x$ represents a hydrogen atom or a straight or branched chain alkyl group having from 1 to 4 carbon atoms, especially a methyl, ethyl or t-butyl group, or represents a phenyl group or a phenoxyalkyl group in which the alkyl moiety is straight-chained or branched and has up to 4 carbon atoms, and is especially a methyl group.

An ester group at the 8-position may be the only ester group present, or it may present in addition to an ester group at the 2-carboxyl group. An ester group may be introduced at the 8-hydroxy group using an organic acid or a derivative thereof by those methods described above in connection with esterification of the 2-carboxy group with an alcohol. A particularly convenient method is to react a compound of formula I or an ester thereof of formula Ia with an activated acid derivative, for example, an acid anhydride. In this case, it is advantageous to carry out the reaction in the presence of a catalyst, for example, 4-dimethylaminopyridine.

A compound of formula IV may be produced as shown in the following Reaction Scheme I:

Reaction Scheme I

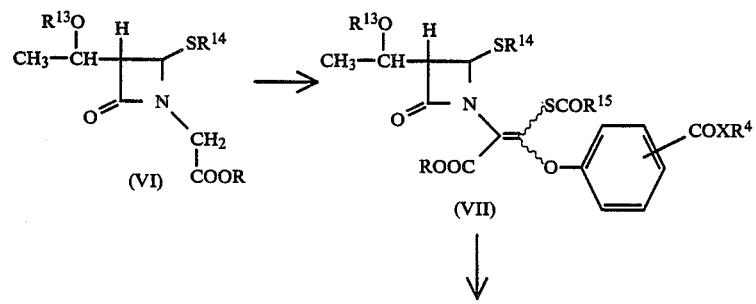

-continued
Reaction Scheme I

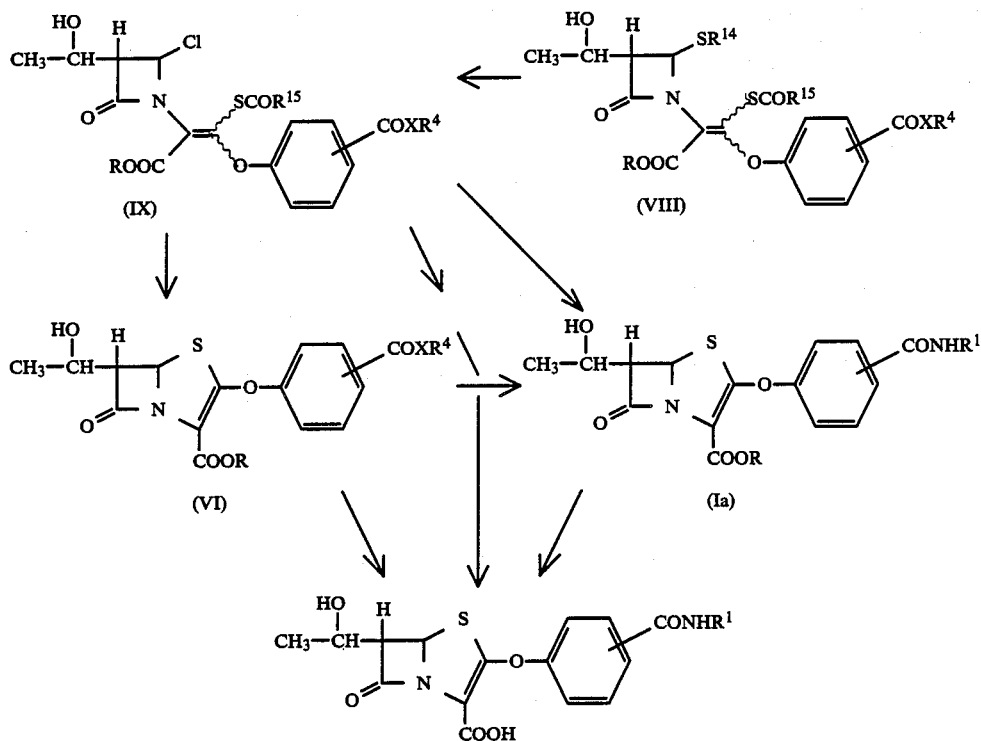

In Reaction Scheme I, X, R, $R^1$ and $R^4$ are as defined above, and preferred meanings for $R^4$ are as given above; $R^{13}$ represents a hydrogen atom or a hydroxy protecting group, and $R^{14}$ and $R^{15}$ each independently represents a phenyl group or an alkyl group having up to 4 carbon atoms.

Compound VI is reacted, in the presence of a base, with a compound of formula X

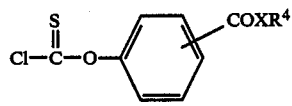

in which X and $R^4$ are as defined above, followed by reaction with an activated carboxylic acid derivative which comprises the group $R^{15}$ as defined above, for example, with an acyl halide of formula XI

in which $R^{15}$ is as defined above and $R^{16}$ represents a chlorine or bromine atom.

While many phenyl chlorothionoformates are known, certain compounds of formula X have not been described before; they may be prepared by methods analogous to those described for the preparation of known compounds, see for example, Rivier & Schalch, Helv. Chem. Acta., Vol 6, 1923, p605, and Reich & Martin, Chem. Berichte, Vol 98, 1965, p2063.

The reaction between compound X and compound VI is carried out in the presence of a base, preferably having a $pK_a > 20$, preferably a metallated amine, and examples of preferred bases are lithium diisopropylamide, lithium hexamethyldisilazide, lithium 2,2,6,6-tetramethylpiperidide, lithium cyclohexyl isopropylamide, and sodamide.

The reaction is generally carried out in an aprotic solvent, for example, an oxygenated hydrocarbon, preferably an ether, for example, diethyl ether, tetrahydrofuran, dioxane, glyme or diglyme. The reaction temperature is, for example from $-120°$ to $+30°$ C., preferably from $-78°$ to $-20°$ C.

The amount of base used is, for example, from 1 to 3 moles, calculated per mole of compound VI, preferably from 1.5 to 2.5 moles of base. The compound of formula X is preferably used in an amount of from 1 to 1.5 moles per mole of compound VI, preferably from 1 to 1.1 moles of compound X per mole of compound VI.

The reaction may be carried out as follows: The base may be added to a stirred solution of compounds VI and X. Alternatively, to a stirred solution of compound VI under an inert atmosphere is added the base and subsequently a solution of compound X in the same or a different solvent.

The activated acid derivative, preferably of formula XI, is preferably added to the mixture resulting from the reaction of compounds VI and X, especially in an amount of from 1 to 2 moles calculated on compound VI. The reaction is preferably carried out at a temperature of from $-40°$ to $40°$ C., adding the compound of formula XI to the reaction mixture at the temperature at which the reaction between compounds VI and X took place, and then warming, or working-up at this temperature.

The —$SCOR^{15}$ group in the resulting compound of formula VII may be E or Z to the —COOR group. (The terms E and Z are as defined on page 142 of Allinger et al, "Organic Chemistry" 1971, Worth, N.Y.) The isomers may be separated for the subsequent reaction, but this is not generally necessary, and the ismmeric mixture is generally used as both isomers give a compound of formula I.

It is preferable that $R^{13}$ in compound VI represents a hydroxy protecting group to prevent the hydroxy group from reacting with the compound of formula X. The protective group is then removed from compound VII in order to obtain the desired 5R stereochemistry in the final product. The protective group may be removed in any conventional manner to give compound VIII. Preferred hydroxy-protecting groups $R^{13}$ are those that are compatible with the synthesis of the compound of formula VII and which may be removed under conditions in which the resulting compound VIII is stable. Compound VIII has been found to be substantially stable in the presence of a proton source, for example, hydrogen chloride, aqueous hydrochloric acid or aqueous hydrofluoric acid. Accordingly, one type of preferred hydroxy protecting group $R^{13}$ is that which can be removed under acidic conditions. Such gruups are well known in the art and are, for example, tetrahydropyranyl and tetrahydrofuranyl groups; acetal and ketal groups, for example, of formula

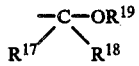

in which $R^{17}$ and $R^{18}$, which may be the same or different, each represents a hydrogen atom or a lower alkyl group, preferably a methyl group, or $R^{17}$ and $R^{18}$ together with the carbon atoms to which they are attached, represent a cycloalkyl ring having from 4 to 7 carbon atoms, and $R^{19}$ represents a lower alkyl group, preferably a methyl or ethyl group, or $R^{17}$ and $R^{19}$, together with the carbon atom and the oxygen atom to which they are attached, respectively, represent a tetrahydropyranyl ring; also silyl ethers, for example, having three substituents on the silicon atom, and preferably up to 24 carbon atoms in total, the three substituents being the same or different, and selected from alkyl, alkenyl and cycloalkyl groups, and phenyl and phenalkyl groups which may be unsubstituted or substituted as defined above, for example, —$SiR^8R^9R^{10}$ groups, in which $R^8$, $R^9$ and $R^{10}$ are as defined above, that is to say, they may be the same or different, and each represents a lower alkyl group or a phenyl group, for example, giving trimethylsilyl, triethylsilyl, diphenyl-t-butylsilyl, dimethyl-t-butylsilyl, and methyldiphenylsilyl groups; and stannyl groups, for example, having up to 24 carbon atoms and three substituents, which may be the same or different, selected from alkyl, alkenyl, cycloalkyl, alkoxy and phenoxy groups, and phenyl and phenalkyl groups which may be unsubstituted or substituted, for example, groups of the formula $SnR^{20}R^{21}R^{22}$, in which $R^{20}$, $R^{21}$ and $R^{22}$, which may be the same or different, each represents a lower alkyl group, for example, a tri-n-butylstannyl group. (The term "lower" is used in the present specification to denote groups having up to 4 carbon toms.)

Preferred $R^{13}$ groups are tetrahydropyranyl, 2-methoxyprop-2-yl, trimethylsilyl and, especially, triethylsilyl and t-butyldimethylsilyl groups.

Such groups may be removed by acid hydrolysis, for example, using 0.1 to 2M, preferably 0.5M hydrochloric acid, for example, 6M HCl in, for example, tetrahydrofuran, cf. Belgian Patent Specification No. 881 012; n-Bu$_4$NF in an acidic medium, for example, in acetic acid, cf. Belgian Patent Specification No. 882 764; or aqueous hydrogen fluoride, for example, in the presence of acetonitrile, cf. J. Chem. Soc. Perkin 1, 1981, 2055.

The resulting compound VIII having a free hydroxy group is then chlorinated using an agent capable of splitting a carbon-sulphur bond and of introducing a chlorine atom. Such agents are well known in the art and include, for example, molecular chlorine, sulphuryl chloride, t-butyl hypochlorite and cyanogen chloride.

The reaction is generally carried out at a temperature within the range of from $-60°$ to $+20°$ C. The reaction is generally carried out in a solvent or diluent that is non-protic, and is inert under the reaction conditions, for example, an ether, a hydrocarbon or a halogenated hydrocarbon, for example, dioxane, benzene, chloroform or methylene chloride. A mixture of two or more solvents may be used. Examples of halogenating systems are: chlorine in chloroform, chlorine in benzene and t-butyl hypochlorite in benzene. In the latter two cases, the temperature is preferably from 5° to 20° C., and normally from 5° to 10° C. Generally, 1 to 2 moles of chlorine are used per mole of compound VIII, cf. S. Kukolja, J. Amer. Chem. Soc. (1971), 93, 6267 and P. C. Cherry, C. E. Newall and N. S. Watson, J.C.S. Chem. Comm. 1979 p. 663.

The resulting compound of formula IX may be converted into a compound of formula IV in the presence of a base. The base used for this reaction should not affect the —$COXR^4$ group. The base may be inorganic or organic, and may be chosen, for example, from ammonia, or an alkali metal, especially a sodium or potassium, carbonate, bicarbonate, or hydroxide; a primary amine, for example, methylamine, etyylamine, aniline or benzylamine; an alkali metal alkoxide, for example, sodium methoxide; or a heterocyclic base, for example, having a $pK_a$ within the range of from 5 to 9, for example, imidazole, pyridine or a substituted pyridine, for example, an alkyl, amino or alkylamino-substituted pyridine, for example, 4-methylpyridine or 4-dimethylaminopyridine. Imidazole is particularly preferred.

The reaction is generally carried out in a solvent or diluent, the choice of which is wide, provided that it is inert under the reaction conditions. Examples of solvents and diluents are oxygenated hydrocarbons, for example, alcohols, for example, having up to 4 carbon atoms, for example, ethanol; ethers, for example, having up to 4 carbon atoms, for example, diethyl ether, also tetrahydrofuran and dioxane; ketones, for example, having up to 4 carbon atoms, for example, acetone and methyl ethyl ketone; esters, for example, methyl acetate and ethyl acetate; and amides, for example, dimethylformamide and dimethylacetamide; also chlorinated hydrocarbons, for example, chloroform, methylene chloride and carbon tetrachloride; aromatic hydrocarbons, for example, benzene and toluene; and other solvents for example, acetonitrile and nitromethane. A mixture of two or more solvents may be used, and solvents are preferably used in admixture with water, preferably a water-miscible solvent is used in admixture with 5 to 20% (v/v) water.

The reaction is generally carried out at a temperature within the range of from 0° to 40° C., preferably from 0 to 20° C.

A compound of formula IV may be converted into a compound of formula I or Ia as described above.

As mentioned above, if the base that is reacted with compound IX is an amine of formula III

R¹NH₂    III

A compound of formula I or an ester of formula Ia may be prepared as shown in the following Reaction Scheme II:

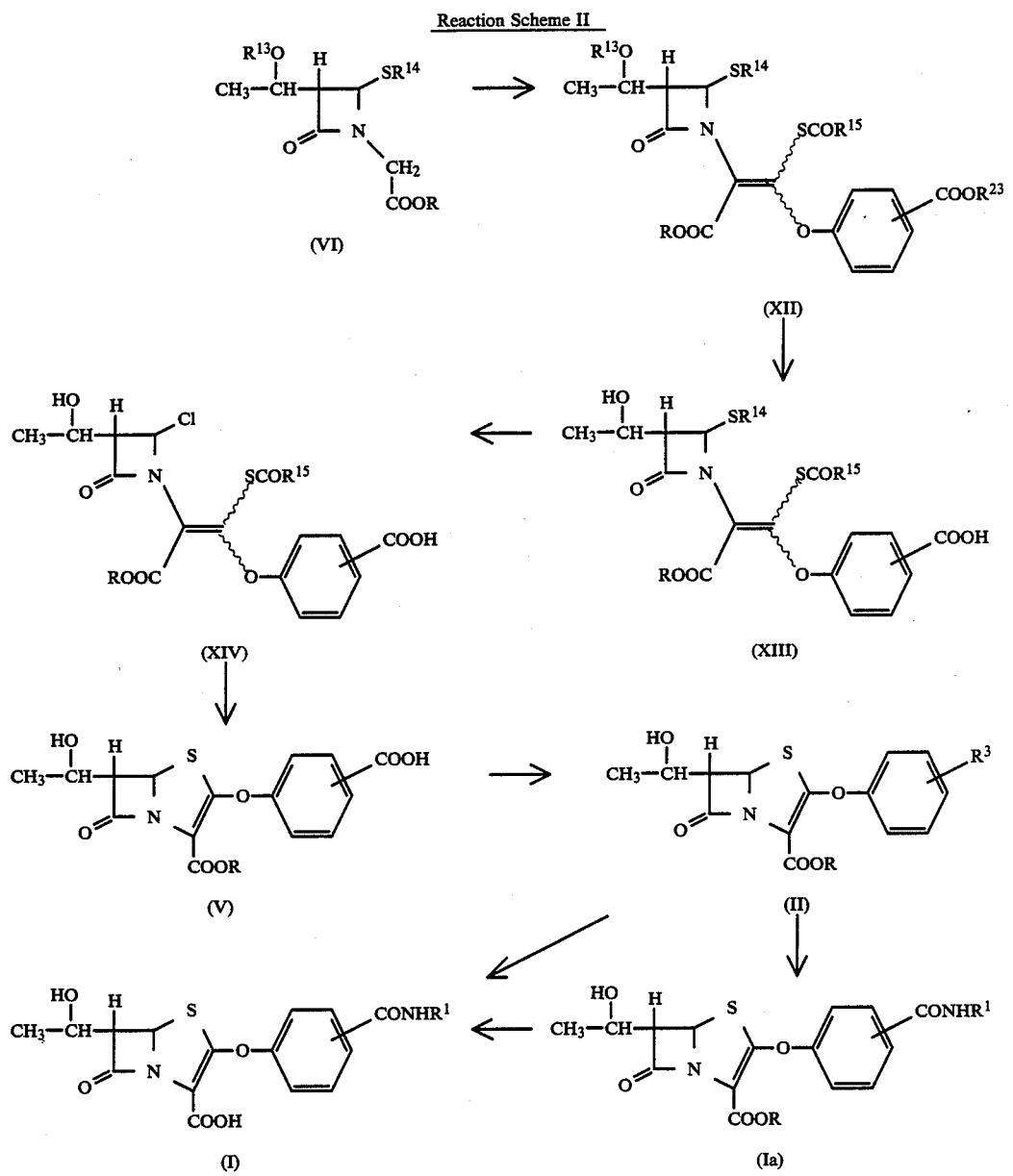

in which R¹ is as defined above, then compound IX can be converted directly into compound I or Ia. In this case it is generally necessary to use two or more moles of the amine of formula III per mole of compound IX. For direct conversion to compound I or Ia, R⁴ in compound IX preferably represents a 4-chlorophenyl or 2,4,5-trichlorophenyl group when X represents a sulphur atom or, especially, represents a pentafluorophenyl group when X represents an oxygen or sulphur atom. Particularly preferred are compounds of formula IX wherein X represents an oxygen atom and R⁴ represents a pentafluorophenyl group.

Compound IX may be converted to compound I or Ia via the in situ formation of compound IV, or the XR⁴ group in compound IX may be displaced by the amine before cyclisation. Both pathways are part of the present invention.

in which R, R¹, R³, R¹³ R¹⁴ and R¹⁵ are as defined above, and R²³ represents a carboxy protecting group.

A compound of formula VI may be converted into a compound of formula XII by reaction, in the presence of a base, with a compound of formula XVI

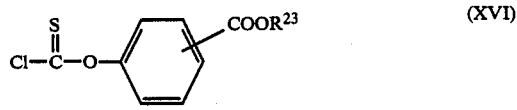    (XVI)

in which R²³ is as defined above, followed by reaction with an activated carboxylic acid derivative which comprises the group R¹⁵, for example, with an acyl halide of formula XI as defined above to give a compound of formula XII. These reactions are carried out as described in Reaction Scheme I for the reaction of the corresponding compounds VI and X followed by reaction with compound XI to give the corresponding compound of formula VII.

In compound XII, $R^{23}$ represents a carboxy protecting group, and it is preferable to use a carboxy protecting group that can be removed under the same conditions as the hydroxy protecting group $R^{13}$, that is to say, preferably under acidic conditions. Examples of such hydroxy protecting groups are given above with reference to compound VII. Preferably $R^{23}$ is a silyl group, for example, as described above for $R^{13}$, and is especially a diphenyl-t-butylsilyl group. Compound XII can thus be converted into compound XIII in one step by the simultaneous removal of the two protecting groups $R^{13}$ and $R^{23}$.

The chlorination of compound XIII may be carried out as described above in Reaction Scheme I for the chlorination of compound VIII, and the resulting compound of formula XIV may be converted into a compound of formula V in the presence of a base, as described above in Reaction Scheme I for the ring closure of compound IX to give compound II.

A compound of formula V may be converted into a compound of formula II and then into a compound of formula I or Ia as described above.

In both of the above Reaction Schemes, in some cases it may be preferable to retain the carboxy protecting group R until after formation of the desired compound of formula Ia. The carboxy protecting group R is as defined above, and preferably represents a p-nitrobenzyl group. In other cases, for example, when a compound of formula IV is used, it may be desirable that R represents a hydrogen atom. A carboxy protecting group R may be removed from the 2-carboxy group at any appropriate point in the reaction sequence.

If desired, an ester group —COOR can be transesterified by ester interchange at any stage of the reaction scheme, and especially after formation of an ester of formula Ia, to give another ester of formula Ia, for example, an ester that can be converted into the free acid of formula I or a carboxylate under physiological conditions. Alternatively, a resulting ester of formula Ia can be converted into the free acid or a salt; a free acid can be esterified or converted into a salt; or a salt can be converted into the free acid, an ester or a different salt. In each case, the salt is especially a physiologically tolerable salt, and an ester is especially one that can be removed under physiological conditions Examples of such procedures are given above.

At each stage of either of the reaction sequences, the desired compound may be isolated from the reaction mixture and, if desired, purified by the appropriate techniques used for the purification of organic compounds, for example, chromatography and crystallisation.

As indicated above, various intermediates may be produced in the form of mixtures of isomers of various kinds. Such mixtures may be separated or resolved at any stage, or an isomeric mixture may be used per se for subsequent reactions.

Chlorination of the 4R-isomer of a compound of formula VIII or XIII gives predominantly the 4S-isomer of compound IX or XIV, respectively. The proportion of 4S:4R-isomers of compound IX or XIV depends on the chlorination agent and reaction conditions used, but in general varies from 3:1 to as high as 18:1. The 4R- and 4S-isomers can be separated readily, for example, by chromatography. A compound of formula IX or XIV also has E/Z isomerism at the double bond, and in some cases, the chlorinated compound of formula IX or XIV is obtained in the form of a substantially pure E or Z isomer. In other cases, an E/Z isomeric mixture is obtained, and the 4R- and 4S-isomers may be separated further into the individual E and Z isomers if desired. It is not generally necessary to separate the E and Z isomers, but it is preferable to separate the 4R- and 4S-isomers before conversion into a compound of formula IV or V, respectively, as the 4S-isomer is converted by reaction with a base into the more desirable 5R-isomer of formula IV or V and, subsequently, of formula I or Ia.

As mentioned above, a compound of formula I may have the R or S stereochemistry independently at positions 5, 6 and 8. Any mixture of two or more isomeric forms may be resolved, if desired, or a compound of formula I can be used in the form of an isomeric mixture. The preferred stereochemistry at position 5 in compound I is generally R, corresponding to that in naturally occurring penicillins and cephalosporins, at position 6 is S and at position 8 is R.

The compounds of formula I, esters thereof at the 2-carboxylic acid group, and salts thereof are $\beta$-lactamase inhibitors, and the compounds are generally stable to the action of $\beta$-lactamases produced by gram positive organisms, for example, *Staphylococcus aureus* and gram negative organisms, for example, *Enterobacter cloacae*. They also possess antibacterial properties themselves and may be used in humans and other animals, for example, to treat bacterial infections caused by gram-positive and gram-negative bacteria, for example, *Staphylococcus aureus, Streptococcus pyogenes, Bacillus subtilis, Escherichia coli, Pseudomonas aeruginosa,* and *Proteus morganii,* some strains of which are penicillin resistant.

It has been found that compounds of formula I (and esters thereof at the 2-carboxylic acid group) having an esterified hydroxy group at the 8-position also have antibacterial and/or $\beta$-lactamase inhibiting properties, in particular since the 8-ester group can be cleaved in vivo by esterases. In addition, esterification at the 8-hydroxy group can enhance the degree of absorption on oral administration.

Compounds of the present formula I are included broadly within the general formula I of our co-pending UK Patent application No. 2 102 798, but the compounds of the present formula I were not specifically disclosed nor manufactured therein. Moreover, compounds of the present formula I have certain advantages with respect to antimicrobial activity compared with the corresponding unsubstituted phenoxy compound of our earlier application, for example, 5R-3-(4-carbamoylphenoxy)-6S-(1R-hydroxyethyl)-7-oxo-4-thia-1-azabicyclo[3,2,0]hept-2-ene-2-carboxylate has greater antibacterial activity against a variety of microorganisms, particularly $\beta$-lactamase producing organisms than does the corresponding unsubstituted 3-phenoxy compound, as shown in the Table below:

The antimicrobial activity was determined by measuring the Minimum Inhibitory Concentration (MIC). The MIC of the compounds was determined by a standard test, the "agar dilution test" according to Lorian (Antibiotics in Laboratory Medicine, Williams and Wilkins, Baltimore/London 1980) as follows:

A two-fold decreasing concentration series of each compound was prepared in Petri dishes containing 15 ml of Mueller Hinton agar (Difco). One Petri dish containing only the Mueller Hinton agar served as control for bacterial growth. Each Petri dish was inoculated with a multi-point inoculator (Denley), which transfered 0.6 μl of a 1:100 diluted 18 hours culture of the appropriate test bacterium. After 16 to 18 hours of incubation at 37° C., the Petri dishes were examined for growth of bacteria. The lowest concentration of the compound which causes complete inhibition of growth is taken as the MIC.

Table of antimicrobial activity

[Structure: 4-thia-1-azabicyclo[3,2,0]hept-2-ene with OH-CH(CH₃)- at position 6, O= at position 7, and -O-phenyl-Rₐ at position 3, COOK at position 2]

| Organism | Minimum Inhibitory Concentration in μg/ml | |
|---|---|---|
| | $R_a = H$ | $R_a = 4\text{-CONH}_2$ |
| Str. pyogenes 77A | 0.05 | 0.05 |
| Str. pyogenes 308 A | 0.05 | 0.025 |
| Str. faecium D | 12.5 | 6.25 |
| Staph. aureus SG 511 | 0.19 | 0.05 |
| Staph. aureus 285 | 0.39 | 0.1 |
| Staph. aureus 503 | 0.39 | 0.1 |
| Bac. subtilis ATCC 6633 | 0.1 | 0.05 |
| E. coli 055 | 3.125 | 0.19 |
| E. coli DC2 | 1.56 | 0.78 |
| E. coli TEM | 12.5 | 0.39 |
| E. coli 1507 E | 1.56 | 0.39 |
| Kl. aerog. 1082 E | 1.56 | 0.39 |
| Kl. aerog. 1522 E | 12.5 | 0.78 |
| Ent. cloacae 1321 E | 12.5 | 0.78 |
| Salm. typhimurium MZ II | 6.25 | 0.78 |
| E. coli KN 126 | 25 | 0.39 |

The present invention accordingly provides a pharmaceutical preparation which comprises a compound of formula I, or a physiological tolerable salt or ester thereof, or a mixture of two or more such substances as active ingredient, in admixture or conjuction with a pharmaceutically suitable carrier. The preparation may also comprise one or more other pharmaceutically active substances, for example another antibacterial substance, especially one having a β-lactam ring. The preparations may be in a form suitable for enteral or parenteral administration, for example, for oral intravenous or intramuscular administration, for example, as tablets, capsules, syrups, or steril injectable or infusion solutions. The preparations are advantageously in unit dosage form and preferably comprise from 10 to 2000 mg of the active ingredient per unit dose. The daily dosage of the active ingredient is generally from 20 to 8000 mg, in divided doses, generally up to 4 doses.

The invention also provides the use of a compound of formula I or a physiologically tolerable ester or salt thereof for the manufacture of a medicament for the treatment of bacterial infections.

The invention further provides a method of treating mammals, especially humans, to combat a bacterial infection, which comprises administering to the mammal a compound of formula I or a physiologically tolerable ester or salt thereof.

The invention further provides a pharmaceutical preparation which comprises an active ingredient as defined above, in unit dosage form.

The invention also provides a pharmaceutical preparation which comprises an active ingredient as defined above, or a physiologically tolerable salt thereof or a mixture of two or more such substances, and one or more further pharmaceutically active substances, in unit dosage form.

Unit dosages are preferably as described above.

Of the compounds of formula I, 3-(4-carbamoylphenoxy)-6-(1-hydroxyethyl)-7-oxo-4-thia-1-azabiyclo[3,2,0]hept-2-ene-2-carboxylic acid and 3-(3-carbamoylphenoxy)-6-(1-hydroxyethyl)-7-oxo-4-thia-1-azabiyclo[3,2,0]hept-2-ene-2-carboxylic acid are preferred, especially the 5R,6S,8R-isomer of each of these compounds, and esters and salts thereof.

The present invention also provides compounds of the general formulae XII, XIII, XIV, III and II.

All the compounds of the present invention may exist in various isomeric forms. With the proviso that in formula I and esters and salts thereof the CONHR¹ group must be present at the 3- or 4-position on the phenyl ring, the invention includes all isomeric forms, either in the form of isolated isomers or of mixtures of any two or more isomers.

The following Examples illustrate the invention, but are not limiting. The expert will appreciate that other compounds of the present invention may be prepared analogously.

EXAMPLE 1

Diphenyl-(2-methylprop-2-yl)silyl-4-hydroxybenzoate

To a solution of 20 g of 4-hydroxybenzoic acid and 10 g of imidazole in 100 ml of dry dimethylformamide at 0° C. was added 40 g of t-butylchlorodiphenylsilane. The mixture was stirred at 0° C. for 30 minutes, then at 20° C. for 18 hours, and then partitioned between diethyl ether and water. The organic layer was washed with water, with 10% aqueous potassium hydrogen carbonate, with water and with brine, and then dried over magnesium sulphate. Evaporation in vacuo of the solvent afforded 47.5 g of the title compound as a crystalline white powder.

$^1$H NMR (CDCl$_3$) δ 1.18 (9H, s); 6.16 (1H, broad s); 6.68 and 7.95 (4H, AA'BB' J8.8 Hz); 7.35–7.50 (6H, m); 7.70–7.90 (4H, m).

EXAMPLE 2

Diphenyl-(2-methylprop-2-yl)silyl 4-chlorothioformyloxybenzoate

To a solution of 40.7 ml of thiophosgene in 300 ml of dry diethyl ether at −78° C. was added dropwise a solution of 20 g of diphenyl-(2-methylprop-2-yl)silyl 4-hydroxybenzoate and 8.5 ml of triethylamine. After having been stirred for a further 30 minutes at −78° C. and 90 minutes at room temperature, the mixture was partitioned between diethyl ether and water. The organic layer was washed with water and brine, was dried over calcium chloride, and then evaporated in vacuo to afford 25.9 g of an orange oil. Crromatography over silica gel and elution with hexane-ethyl acetate mixtures afforded 16.8 g of the title compound.

$^1$H NMR (CDCl$_3$) δ 1.19 (9H, s); 7.26 and 8,24 (4H AA'BB' J8.8 Hz); 7.4–7.6 (6H, m); 7.7–7.9 (4H, m).

EXAMPLE 3

4-Nitrobenzyl 2-(3S-{1R-[dimethyl(2-methylprop-2-yl)silyloxy]ethyl}-4R-ethylthio-azetidin-2-on-1-yl)-3-(4-diphenyl[2-methylprop-2-yl]silyloxycarbonylphenoxy)-3-trimethylacetylthiopropenoate To a stirred solution at −40° C. of 25 g of 4-nitrobenzyl 2-(3S-[1R-dimethyl(2-methylprop-2-yl)silyloxyethyl]-4R-ethylthioazetidin-2-on-1-yl)acetate was added a solution of 35 g of diphenyl-(methylprop-2-yl)silyl 4-chlorothioformyloxybenzoate in 200 ml of dry tetrahydrofuran, followed by a mixture of 155 mmol of n-butyllithium and 155 mmol of hexamethyldisilazane in 200 ml of dry tetrahydrofuran which had been precooled to −78° C. After 5 minutes, 13.8 ml of trimethylacetyl bromide was added and the mixture stirred for a further 60 minutes at −40° C., and then poured directly into a mixture of 500 ml of diethyl ether and 500 ml of 0.1M hydrochloric acid. The aqueous layer was extracted in diethyl ether, and the combined organic extracts were washed with brine, dried over aqueous magnesium sulphate and evaporated in vacuo to afford 50 g of an orange oil. The product was used without further purification.

EXAMPLE 4

4-Nitrobenzyl 3-(4-carboxyphenoxy)-2-(4R-ethylthio-3S[1R-hydroxyethyl]azetidin-2-on-1-yl)-3-trimethylacetylthiopropenoate A mixture of 50 g of 4-nitrobenzyl 2-(3S-[1R-[dimethyl(2-methylprop-2-yl)silyl]oxyethy]-4R-ethylthio-azetidin-2-on-1-yl)-3-(4-{diphenyl[2-methylprop-2-yl]silyloxycarbonyl}phenoxy)-3-trimethylacetylthiopropenoate, 500 ml of tetrahydrofuran and 100 ml of 5.5M hydrochloric acid was stirred at room temperature for 24 hours, and then partitioned between diethyl ether and water. The organic layer was washed with water, and with brine, was dried over anhydrous magnesium sulphate, and evaporated in vacuo. Chromatography of the residue over silica gel, and elution with hexane-ethyl acetate-formic acid mixtures afforded 10.2 g of the title compound.

$\nu_{max}$ (CDCl$_3$) 1765 cm$^{-1}$ $^1$H NMR (CDCl$_3$) δ 1.05 and 1.13 (9H, 2s); 1.20–1.30 (6H, m); 2.6–2.8 (2H, m); 3.27 (1H, dd J2.5 and 4.5 Hz); 4.2–4.4 (1H, m); 5.30 (1H, d J2.5 Hz); 5.31 (2H, AB, J13.5 Hz); 7.10 and 8.03 (4H, AA'BB', J9 Hz); 7.60 and 8.24 (4H, AA'BB' J9 Hz).

EXAMPLE 5

4-Nitrobenzyl 3-(4-carboxyphenoxy)-2-(4S-chloro-3S-[1R-hydroxyethyl]azetidin-2-on-1-yl)-3-trimethylacetylthiopropenoate To a stirred solution of 10 g of 4-nitrobenzyl 3-(4-carboxyphenoxy)-2-(4R-ethylthio-3S- [1R-hydroxyethyl]-azetidin-2-on-1-yl)-3-trimethylacetylthiopropenoate in 60 ml of chloroform at −60° C. was added a solution of 192 mmoles of chlorine in 17.8 ml of carbon tetrachloride. After 30 minutes, the reaction mixture was left to warm to room temperature, and the solvent was then removed in vacuo. Chromatography over silica gel using hexane-ethyl acetate-formic acid mixtures afforded 7.3 g of the title compound as a pale yellow foam.

$\nu_{max}$ (CDCl$_3$) 1787, 1731 cm$^{-1}$ $^1$H NMR (CDCl$_3$) δ 1.06 and 1.10 (9H, 2s); 1.39 (3H, d J6.2 Hz); 3.53 (1H, dd J4.3 and 9.5 Hz); 4.33 (1H, dq J6.2 and 9.5 Hz); 5.30 (2H, s); 6.14 (1H, d J4.3 Hz); 7.10 and 8.09 (4H, AA'BB' J8.8 Hz); 7.56 and 8.25 (4H, AA'BB' J8.7 Hz)

EXAMPLE 6

4-Nitrobenzyl 5R,3-(4-carboxyphenoxy)-6S-(1R-hydroxyethyl)-7-oxo-4-thia-1-azabicyclo[3,2,0]hept-2-ene-2-carboxylate To a stirred solution of 5.3 g of 4-nitrobenzyl 3-(4-carboxyphenoxy)-2-(4S-chloro-3S-[1R-hydroxyethyl]-azetidin-2-on-1-yl)-3-trimethylacetylthiopropenoate in a mixture of 90 ml of dioxane and 10 ml of water at 5° C. was addded 1.78 g of imidazole. After 30 minutes at 5° C., the mixture was warmed to room temperature, and then partitioned between ethyl acetate and water. The organic layer was washed successively with water, 1M-citric acid, water, and brine, was dried over magnesium sulphate, and the solvent removed in vacuo. Chromatography over silica gel using ethyl acetate-hexane-formic acid mixtures afforded 3.2 g of the title compound as a pale yellow solid. Further purification by crystallisation from ethyl acetate yielded 1.8 g of a white solid.

$\nu_{max}$ (CDCl$_3$ 1788, 1794(sh) cm$^{-1}$ $^1$H NMR (CDCl$_3$) δ 1.39 (3H, d J6.3 Hz); 3.83 (1H, dd J1.4 and 6.7 Hz); 4.30 (1H, m); 5.21 and 5.40 (2H, AB J13.7 Hz); 5.71 (1H, d J1.4 Hz); 7.20 and 8.11 (4H, AA'BB' J8.9 Hz); 7.51 and 8.18 (4H, AA'BB' J8.8 Hz).

EXAMPLE 7

4-Nitrobenzyl 5R,3-(4-benzotriazol-1-yloxycarbonylphenoxy)-6S-(1R-hydroxyethyl)-7-oxo-4-thia-1-azabicyclo[3,2,0]hept-2-ene-2-carboxylate To a solution of 1 g of 4-nitrobenzyl 5R,3-(4-carboxyphenoxy)-6S-(1R-hydroxyethyl)-7-oxo-4-thia-1-azabicyclo[3,2,0]hept-2-ene-2-carboxylate in 8 ml of dry acetonitrile was added a solution of 420 mg of 1-hydroxybenzotriazole hydrate in 1 ml of tetrahydrofuran, followed after 5 minutes by a solution of 1.02 g of redistilled dicyclohexylcarbodiimide in 2 ml of acetonitrile. The mixture was stirred for 60 minutes, and was then filtered. The filtrate was evaporated in vacuo and the residue chromatographed on silica gel. Elution with hexane-ethyl acetate mixtures and evaporation in vacuo afforded a solid which was dissolved in 5 ml of ethyl acetate and the solution cooled to 0° C. The material which crystallised out was filtered and washed with a little hexane-ethyl acetate mixture to afford 650 mg of the title compound. A further 300 mg of the title compound was obtained by concentration of the mother liquors.

$^1$H NMR (CDCl$_3$) δ 1.41 (3H, d J6.3 Hz); 3.88 (1H, dd J1.5 and 6.6 Hz); 4.32 (1H, m); 5.22 and 5.43 (2H, AB J13.7 Hz); 5.77 (1H, d J1.5 Hz); 7.33 (4H, AA'BB', J8.8 Hz); 7.4–7.7 (5H, m); 8.11 (1H, d J8.4 Hz); 8.32 (2H, d J9.0 Hz).

EXAMPLE 8

4-Nitrobenzyl 5R,6S-(1R-hydroxyethyl)-7-oxo-3-(4-propylcarbamoylphenoxy)-4-thia-1-azabicyclo-[3,2,0]hept-2-ene-2-carboxylate Method A To a stirred solution of 100 mg of 4-nitrobenzyl 5R,3-(4-carboxyphenoxy)-6S-(1R-hydroxyethyl)-7-oxo-4-thia-1-azabicyclo[3,2,0]hept-2-ene-2-carboxylate in 5 ml of dry dichloromethane at −20° C. was added 27 μl of N-methylmorpholine, followed by 32.8 μl of pivaloyl bromide. After 30 mniutes, 40.4 μl of n-propylamine was added, and the mixture warmed to room temperature. The mixture was worked up as follows: the mixture was partitioned between water and dichloromethane; the organic layer was washed with 1M-citric acid, with water, with saturated aqueous sodium hydrogen carbonate, with brine, and was dried over anhydrous magnesium sulphate. Evaporation in vacuo, and chromatography of the residue over silica gel with elution with hexane-ethyl acetate mixtures afforded 20 mg of the title compound.

$v_{max}$ (CH$_2$Cl$_2$ 1784 cm$^{-1}$ $^1$H NMR (DMSO-d$_6$) δ 0.89 (3H, t J7.4 Hz); 1.16 (3H, d J6.2 Hz); 1.52 (2H, m); 3.20 (2H, m); 3.91 (1H, dd J1.2 and 5.8 Hz); 4.01 (1H, m) 5.23 (1H, d J4.6 Hz); 5.27 and 5.40 (2H, AB J14.3 Hz); 5.77 (1H, d J1.2 Hz); 7.35 and 7.89 (4H, AA'BB' J8.7 Hz); 7.57 and 8.17 (4H, AA'BB' J8.7 Hz); 8.49 (1H, t J5.3 Hz).

Method B

To a stirred suspension of 100 mg of 4-nitrobenzyl 5R,3-(4-carboxyphenoxy)-6S-(1R-hydroxyethyl)-7-oxo-4-thia-1-azabicyclo[3,2,0]hept-2-ene-2-carboxylate in 5 ml of dry dichloromethane at −20° C. was added 22.6 μl of N-methylmorpholine, followed after 5 minutes by 39.2 μl of diphenylphosphinyl chloride. After 30 minutes at −20° C., 22.6 μl of N-methylmorpholine and 16.9 μl of n-propylamine were added and the mixture was stirred for a further 30 minutes at −20° C., and was then worked up as described in Method A to afford 20 mg of the title compound as a pale yellow viscous oil.

Method C

To a stirred suspension of 100 mg of 4-nitrobenzyl 5R,3-(4-carboxyphenoxy)-6S-(1R-hydroxyethyl)-7-oxo-4-thia-1-azabicyclo[3,2,0]hept-2-ene-2-carboxylate in 5 ml of dry dichloromethane at −20° C. was added 27 μl of N-methylmorpholine, followed after 5 minutes by 32.8 μl of trimethylacetyl bromide. After 30 minutes at −20° C., 27 μl of N-methylmorpholine and 20.2 μl of n-propylamine were added and the mixture was stirred for a further 30 minutes at −20° C., and was then worked up as described in Method A to afford 30 mg of the title compound as a pale yellow viscous oil.

EXAMPLE 9

Potassium 5R,6S-(1R-hydroxyethyl)-7-oxo-3-(4-propylcarbamoylphenoxy)-4-thia-1-azabicyclo[3,2,0]hept-2-ene-2-carboxylate A mixture of 46 mg of 4-nitrobenzyl 5R,6S-(1R-hydroxyethyl)-7-oxo-3-(4-propylcarbamoylphenoxy)-4-thia-1-azabicyclo[3,2,0]hept-2-ene-2-carboxylate, 8.7 mg of potassium hydrogen carbonate, 132 mg of 5% palladium on charcoal, 10 ml of ethyl acetate and 10 ml of water was hydrogentaed at 345 kPa (50 psi) for 90 minutes and then filtered through diatomaceous earth ("Hiflo", Trade Mark). The aqueous layer was separated and lyophilised to afford 30 mg of the title compound.

$^1$H NMR (DMSO-d$_6$) δ 0.87 (3H, t J7.3 Hz); 1.15 (3H, d J6.3 Hz); 1.5 (2H, m); 3.15 (2H, m); 3.58 (1H, dd J1 and 7.5 Hz); 3.91 (1H, m); 5.58 (1H, d J1 Hz); 7.10 and 7.82 (4H, AA'BB' J8.6 Hz); 8.39 (1H, broad m).

EXAMPLE 10

4-Nitrobenzyl 5R,3-(4-carbamoylphenoxy)-6S-(1R-hydroxyethyl)-7-oxo-4-thia-1-azabicyclo[3,2,0]hept-2-ene-2-carboxylate To a stirred solution of 900 mg of 4-nitrobenzyl 5R,3-(4-(benzotriazol-1-yl)oxycarbonylphenoxy)-6S-(1R-hydroxyethyl)-7-oxo-4-thia-1-azabicyclo[3,2,0]hept-2-ene-2-carboxylate in 5 ml of tetrahydrofuran was added 228 μl of triethylamine, followed after 5 minutes by a solution of 126 mg of ammonium acetate in 200 μl of water. After the mixture had been stirred for a further 30 minutes, the precipitate was filtered off and washed with ethyl acetate and acetonitrile to afford 300 mg of the title compound. A further 100 mg of product was obtained from the mother liquors m.p. 145° C. (dec)

$^1$H NMR (DMSO-d$_6$) δ 1.15 (3H, d J6.2 Hz); 3.90 (1H, dd J1.4 and 5.9 Hz); 4.00 (1H, m); 5.25 (1H, broad s); 5.28 and 5.40 (2H, AB, J14.2 Hz); 5.77 (1H, d J1.4 Hz); 7.33 and 7.91 (4H, AA'BB' J8.8 Hz); 7.44 (1H, broad s); 7.56 and 8.16 (4H, AA'BB' J8.8 Hz); 8.02 (1H, broad s).

EXAMPLE 11

Potassium 5R,3-(4-carbamoylphenoxy)-6S-(1R-hydroxyethyl)-7-oxo-4-thia-1-azabicyclo[3,2,0]hept-2-ene-2-carboxylate A mixture of 340 mg of 4-nitrobenzyl 5R,3-(4-carbamoylphenoxy)-6S-(1R-hydroxyethyl)-7-oxo-4-thia-1azabicyclo[3,2,0]hept-2-ene-2-carboxylate, 340 mg of 10% palladium on charcoal, 10 ml of dioxane, 72.9 mg of potassium hydrogen carbonate and 10 ml of water was hydrogenolysed at 345 kPa (50 psi) for 60 minutes, and then filtered through diatomaceous earth. Lyophilisation of the filtrate afforded 280 mg of a yellowish solid, which was dissolved in water and extracted with ethyl acetate. Lyophilisation of the aqueous layer afforded 255 mg of the title product as an off-white solid. m.p. 159° C. (dec)

$^1$H NMR (D$_2$O) δ 1.32 (3H, d J6.4 Hz); 3.98 (1H, dd J1.3 and 6.0 Hz); 4.28 (1H, m); 5.74 (1H, d J1.3 Hz); 7.33 and 7.87 (4H, AA'BB' J8.8 Hz).

EXAMPLE 12

4-Nitrobenzyl 5R,6S-(1R-hydroxyethyl)-3-(4-methylcarbamoylphenoxy)-7-oxo-4-thia-1-azabicyclo[3,2,0]hept-2-ene-2-carboxylate To a stirred solution of 200 mg of 4-nitrobenzyl 5R,3-(4-(benzotriazol-1-yl)oxycarbonylphenoxy)-6S-(1R-hydroxyethyl)-7-oxo-4-thia-1-azabicyclo-3,2,0 hept-2-ene-2-carboxylate in 2 ml of dry tetrahydrofuran at 0° C. was added 47.7 μl of triethylamine followed by 26.5 μl of a 40% by weight aqueous solution of methylamine. After 30 minutes at 0° C., and 60 minutes at room temperature, the mixture was partitioned between ethyl acetate and water; the organic layer was washed with 1M-citric acid, with brine, was dried over anhydrous magnesium sulphate and evaporated in vacuo. Chromatography of the residue over silica gel, and elution with hexane-ethyl acetate mixtures afforded 95 mg of the title compound.

$v_{max}$ (CDCl$_3$) 1780 cm$^{-1}$ $^1$H NMR (CDCl$_3$) δ 1.38 (3H, d J6.3 Hz); 3.02 (3H, d J4.9 Hz); 3.79 (1H, dd J1.5 and 6.7 Hz); 4.3 (1H, m); 5.22 and 5.41 (2H, AB J14.4 Hz); 5.67 (1H, d J1.5 Hz); 6.15

(1H, broad s); 7.18 and 7.77 (4H, AA'BB' J8.8 Hz); 7.53 and 8.17 (4H, AA'BB' J8.8 Hz).

EXAMPLE 13

Potassium 5R,6S-(1R-hydroxyethyl)-3-(4-methylcarbamoyl-phenoxy)-7-oxo-4-thia-1-azabicyclo[3,2,0]hept-2-ene-2-carboxylate A mixture of 196 mg of 4-nitrobenzyl 5R,6S-(1R-hydroxyethyl)-3-(4-methylcarbamoylphenoxy)-7-oxo-4-thia-1-azabicyclo[3,2,0]hept-2-ene-2-carboxylate, 40.4 mg of potassium hydrogen carbonate, 10 ml of ethyl acetate, 10 ml of water and 392 mg of 10% palladium on charcoal was hydrogenated at about 345 kPa (50 psi) for 100 minutes, was then filtered through diatomaceous earth. The aqueous layer was separated and lyophilised to afford 131 mg of a crude product. An aqueous solution of this product was acidified at 0° C. to pH2, and traces of insoluble material removed by filtration. Lyophilisation of the filtrate afforded 116 mg of the product, which was dissolved in water. 31.9 Mg of potassium hydrogen carbonate was added and the solution refiltered through diatomaceous earth, and lyophilised to afford 112 mg of the title compound. $^1$H NMR (D$_2$O) δ 1.29 (3H, d J6.4 Hz); 2.91 (3H, s); 3.94 (1H, dd J1 and 5 Hz); 4.25 (1H, m); 5.71 (1H, d J1 Hz); 7.29 and 7.77 (4H, AA'BB' J8.8 Hz).

EXAMPLE 14

Diphenyl-(2-methylprop-2-yl)silyl 3-hydroxybenzoate

To stirred solution of 50.4 g of 3-hydroxybenzoic acid in 200 ml of dry dimethylformamide at 0° C. was added 24.85 g of imidazole, followed by 100 g of diphenyl-(2-methylprop-2-yl)silyl chloride. The mixture was stirred at room temperature for 16 hours, and partitioned between ethyl acetate and cold water. The organic layer was washed with water, with an aqueous potassium hydrogen carbonate solution and with brine, was dried over anhydrous magnesium sulphate and evaporated to dryness. The resulting white solid was slurried in dry chloroform and filtered to afford 72 g of the title compound.

$^1$H NMR (acetone-d$_6$) δ 1.18 (9H, s); 6.8–7.9 (14H, m); 8.7 (1H, broad s).

EXAMPLE 15

Diphenyl-(2-methylprop-2-yl)silyl 3-chlorothioformyloxybenzoate

To a stirred solution of 130 ml of thiophosgene in 250 ml of dry diethyl ether at −78° C. was added dropwise a mixture of 72 g of diphenyl- (2-methylprop-2-yl)silyl 3-hydroxybenzoate and 29 ml of triethylamine in 200 ml of dry diethyl ether. The mixture was stirred at −78° C. for 30 minutes, at room temperature for 120 minutes, and then partitioned between diethyl ether and water. The organic layer was washed with cold water and with brine, and was dried over anhydrous calcium chloride. Evaporation in vacuo, and repeated addition of dry diethyl ether and re-evaporation in vacuo afforded 86.5 g of the title compound as a viscous orange oil.

$^1$H NMR (CDCl$_3$) δ 1.20 (9H, s); 7.35–7.55 (7H, m); 7.54 (1H, t J7.8 Hz); 77.74 (4H, dm J 6 Hz); 7.90 (1H, dd J2.2 and 1.6 Hz); 8.11 (1H, dm J7.8 Hz).

EXAMPLE 16

4-Nitrobenzyl 2-(3S-{1R-[dimethyl(2-methylprop-2-yl)silyloxy]ethyl}-4R-ethylthioazetidin-2-on-1-yl)-3-(3-diphenyl-[2-methylprop-2-yl]silyloxycarbonyl phenoxy)-3-trimethylacetylthiopropenoate By a procedure analogous to that described in Example 3, and using 15 g of 4-nitrobenzyl 2-(3S-{1R[dimethyl(2-methylprop-2-yl)silyloxy]ethyl}-4R-ethylthioazetidin-2-on-1-yl)acetate, 17 g of diphenyl(2-methylprop-2-yl)silyl 3-chlorothioformyloxybenzoate, 70 mmol of n-butyllithium, 14.7 ml of hexamethyldisilazane, 750 ml of dry tetrahydrofuran, and 11.4 ml of trimethylacetyl bromide there was obtained 40 g of the title compound as an orange oil, which was used without further purification.

$v_{max}$ (film) 1710 and 1765 cm$^{-1}$ $^1$H NMR (CDCl$_3$) δ 0.05 (6H, s); 0.83 (9H, s); 0.91 (9H, s); 1.04 and 1.11 (9H, 2s); 1.2–1.4 (6H, m); 2.5–2.9 (2H, m); 3.3 (1H, m); 4.35 (1H, m); 5.36 (2H, m); 5.48 (1H, d J2Hz); 7.3–8.4 (18H, m).

EXAMPLE 17

4-Nitrobenzyl 3-(3-carboxyphenoxy)-2-(4R-ethylthio-3S-[1R-hydroxyethyl]azetidin-2-on-1-yl)-3-trimethylacetylthiopropenoate A mixture of 40 g of 4-nitrobenzyl 2-(3S- 1R[dimethyl-(2-methylprop-2-yl)silyloxy]ethyl -4R-ethylthioazetidin-2-on-1-yl)-3-(3- diphenyl[2-methylprop-2-yl]silyloxycarbonyl phenoxy)-3-trimethylacetylthiopropenoate, 150 ml of tetrahydrofuran, and 44 ml of 5.5M-hydrochloric acid was stirred at room temperature for 16 hours, and was then partitioned between ethyl acetate and water. The organic layer was washed with water and with brine, was dried over anhydrous magnesium sulphate, and was evaporated in vacuo. Chromatography of the residue over silica gel, and elution with hexane-ethyl acetate-formic acid mixtures afforded 6.0 g of the title product as an E/Z mixture.

$v_{max}$ 1735, 1715(sh), 1770(sh), 3450 cm$^{-1}$ $^1$H NMR (CDCl$_3$) δ 1.00 and 1.07 (9H, 2s); 1.2–1.4 (6H, m) 2.6–2.9 (2H, m); 3.28 (1H, dd J2.7 and 4.4 Hz); 4.3 (1H, m); 5.32 (2H, AB J13.5 Hz); 5.37 (1H, d J2.7 Hz); 7.29 (1H, m); 7.37 (1H, dd J2 and 7.8 Hz); 7.59 and 7.40 (2H, AA'BB' J7.8 Hz); 7.71 (1H, m); 7.86 (1H, dm J7.8 Hz); 8.08 and 8.22 (2H, AA'BB' J7.8 Hz).

EXAMPLE 18

4-Nitrobenzyl 3-(3-carboxyphenoxy)-2-(4S-chloro-3S-(1R-hydroxyethyl)azetidin-2-on-1-yl)-3-trimethylacetylthiopropenoate To a stirred solution of 5.5 g of 4-nitrobenzyl 3-(3-carboxyphenoxy)-2-(4R-ethylthio-3S-[1R-hydroxyethyl]azetidin-2-on-1-yl)-3-trimethylacetylthiopropenoate in 50 ml of dry deuterochloroform at −40° C. was added a solution of 10.6 mmol of chlorine in carbon tetrachloride. The mixture was stirred for a further 30 minutes at −40° C., and for 30 minutes at room temperature, and was evaporated in vacuo. Chromatography of the residue over silica gel, and elution with hexane-ethyl acetate-formic acid mixtures afforded 4.6 g of the title compound.

$v_{max}$ (CDCl$_3$) 1700, 1730, 1783 cm$^{-1}$

¹H NMR (CDCl₃) δ 1.03 and 1.07 (9H, 2s); 1.40 (3H, d J6.4 Hz); 3.55 (1H, m); 4.4 (1H, m); 5.32 (1H, s); 6.15 and 6.20 (1H, 2d J4.2 Hz); 7.29 (1H, m); 7.4–7.7 (3H, m); 7.74 (1H, m); 7.9–8.05 (1H, m); 8.12 and 8.24 (2H, 2d J8.8 Hz).

EXAMPLE 19

4-Nitrobenzyl 5R,3-(3-carboxyphenoxy)-6S-(1R-hydroxyethyl)-7-oxo-4-thia-1-azabicyclo[3,2,0]hept-2-ene-2-carboxylate To a stirred solution of 2.02 g of 4-nitrobenzyl 3-(3-carboxyphenoxy)-2-(4S-chloro-3S-(1R-hydroxyethyl)azetidin-2-on-1-yl)-3-trimethyl-acetylthiopropenoate in 80 ml of a mixture of dioxane and water (9:1 v/v) at 5° C. was added 682 mg of imidazole. The mixture was stirred for a further 30 minutes at 5° C., and was then partitioned between ethyl acetate and water. The aqueous layer was acidified to pH2 by the addition of 1M-citric acid, and extracted with ethyl acetate. The combined organic layers were washed with 1M-citric acid, with water and with brine, were dried over anhydrous magnesium sulphate and evaporated in vacuo. The residue was chromatographed over silica gel; elution with hexane-ethyl acetate-formic acid mixtures afforded 992 mg of the title compound as a pale yellow foam.

$\nu_{max}$ (CDCl₃) 1710, 1788 cm⁻¹

¹H NMR (CDCl₃) δ 1.38 (3H, d J6.4 Hz); 3.81 (1H, dd J1.4 and 6.7 Hz); 4.3 (1H, m); 5.24 and 5.43 (2H, AB J13.8 Hz); 5.69 (1H, d J1.4 Hz); 7.38–7.5 (2H, m); 7.55 and 8.18 (4H, AA'BB' J8.8 Hz); 7.85 (1H, m); 7.99 (1H, m).

EXAMPLE 20

4-Nitrobenzyl 5R,3-(3-{benzotriazol-1-yl}oxycarbonylphenoxy)-6S-(1R-hydroxyethyl)-7-oxo-4-thia-1-azabicyclo[3,2,0]hept-2-ene-2-carboxylate To a stirred solution of 200 mg of 4-nitrobenzyl 5R,3-(3-carboxyphenoxy)-6S-(1R-hydroxyethyl)-7-oxo-4-thia-[-1-azabicyclo[3,2,0]hept-2-ene-2-carboxylate in 8 ml of acetonitrile at room temperature was added a solution of 111 mg of 1-hydroxybenzotriazole hydrate in 4 ml of tetrahydrofuran, followed after 5 minutes by a mixture of 158 mg of 1-(3-dimethylaminopropyl)-3-ethylcarbodiimide hydrochloride, 2 ml of acetonitrile and 2 ml of tetrahydrofuran. The mixture was stirred for 3 hours at room temperature; filtration afforded 17 mg of the title compound. The filtrate was partitioned between ethyl acetate and water; the organic layer was washed with water, dried over anhydrous magnesium sulphate and evaporated in vacuo to afford a further 172 mg of the title compound as a pale yellow solid.

¹H NMR (DMSO-d₆) δ 1.16 (3H, d J6.2 Hz); 3.91 (1H, dd J1.0 and 5.7 Hz); 4.02 (1H, m); 5.2 (1H, d J4.4 Hz); 5.28 and 5.41 (2H, AB J14.2 Hz); 5.77 (1H, d J1.0 Hz); 7.4–8.0 (9H, m); 7.98 (1H, d J8.6 Hz); 8.18 (2H, d J8.7 Hz).

EXAMPLE 21

3-[5R,6S-(1R-hydroxyethyl)-2-(4-nitrobenzyloxycarbonyl)-7-oxo-4-thia-1-azabicyclo[3,2,0]hept-2-en-3-yl]oxybenzoic anhydride To a stirred solution of 100 mg of 4-nitrobenzyl 5R,3-(3-carboxyphenoxy)-6S-(1R-hydroxyethyl)-7-oxo-4-thia-1-azabicyclo[3,2,0]hept-2-ene-2-carboxylate in 4 ml of acetonitrile was added 79 mg of 1-(3-dimethylaminopropyl)3-ethylcarbodiimide hydrochloride. After stirring for 20 minutes, the mixture was partitioned between ethyl acetate and water; the organic layer was washed with water then with brine, and was then dried over anhydrous magnesium sulphate. Evaporation in vacuo afforded 78 mg of the title compound.

¹H NMR (DMSO-d₆) δ 1.15 33H, d J6.25 Hz); 3.91 (1H, dd J1.3 and 5.9 Hz); 4.01 (1H, m); 5.22 (1H, d J4.6 Hz); 5.29 and 5.42 (2H, ABq J14.4 Hz); 5.76 (1H, d J1.3 Hz); 7.55–8.32 (8H, m)

EXAMPLE 22

4-Nitrobenzyl 5R,6S-(1R-hydroxyethyl)-3-(3-methylcarbamoylphenoxy)-7-oxo-4-thia-1-azabicyclo[3,2,0]hept-2-ene-2-carboxylate Method A To a stirred mixture of 235 mg of 4-nitrobenzyl 5R,3(3- benzotriazol-1-yl oxycarbonylphenoxy)-6S-(1R-hydroxyethyl)-7-oxo-4-thia-1-azabicyclo[3,2,0-]hept-2-ene-2-carboxylate, 8 ml of redistilled dimethylformamide and 53 μl of triethylamine at 0° C. was added 34 μl of a 40% (by weight) solution of methylamine in water. After 30 minutes, the reaction mixture was allowed to warm to room temperature, and was stirred for a further 45 minutes. The mixture was partitioned between ethyl acetate and water; the organic layer was washed with 1M-citric acid, with water, with saturated aqueous sodium hydrogen carbonate, and with brine, was dried over anhydrous magnesium sulphate, and was then evaporated in vacuo. Chromatography of the residue over silica gel, eluting with hexane-ethyl acetate mixtures afforded 94 mg of the title compound.

¹H NMR (CDCl₃) δ 1.35 (3H, d J6.3 Hz); 3.00 (3H, d J4.8 Hz); 3.75 (1H, dd J1.4 and 6.7 Hz); 4.25 (1H, m); 5.21 and 5.41 (2H, AB J13.8 Hz); 5.64 (1H, d J1.4 Hz); 6.19 (1H, m); 7.26–7.65 (6H, m); 8.16 (2H, d J8.8 Hz).

Method B

To a stirred solution of 78 mg of 3-[5R,6S-(1R-hydroxyethyl)-2-(4-nitrobenzyloxycarbonyl)-7-oxo-4-thia-1-azabicyclo[3,2,0]hept-2-en-3-yl]oxybenzoic anhydride in 2 ml of redistilled dimethylformamide was added 15 μl of a 40% by weight aqueous solution of monomethylamine. After 18 hours the mixture was partitioned between ethyl acetate and water; the organic layer was washed with 1M-citric acid, with water, with a saturated sodium hydrogen carbonate solution, with brine; was dried over anhydrous magnesium sulphate and was evaporated in vacuo to yield 33 mg of the title compound.

EXAMPLE 23

4-Nitrobenzyl 5R,3-(3-carbamoylphenoxy)-6S-(1R-hydroxyethyl)-7-oxo-4-thia-1-azabicyclo[3,2,0]hept-2-ene-2-carboxylate To a stirred solution of 139 mg of 4-nitrobenzyl 5R,3-(3- benzotriazol-1-yl oxycarbonylphenoxy)-6S-(1R-hydroxyethyl)-7-oxo-4-thia-1-azabicyclo[3,2,0]hept-2-ene-2-carboxylate, 4 ml of redistilled dimethylformamide and 52 μl of triethylamine was added 27.1 mg of ammonium acetate. After being stirred for a further 90 minutes, the mixture was partitioned between ethyl acetate and water; the organic layer was washed with 1M-citric acid, with water, with a saturated sodium hydrogen carbonate solution, with brine; was dried over anhydrous magnesium sulphate and was evaporated in vacuo to afford 64 mg of the title compound.
$v_{max}$ (CHCl$_3$) 1725 and 1785 cm$^{-1}$
$^1$H NMR (DMSO-d$_6$) δ 1.17 (3H, d J7.2 Hz); 3.89 (1H, m); 4.02 (1H, m); 5.21 (1H, d J4.5 Hz); 5.29 and 5.40 (2H, AB J14.2 Hz); 5.74 (1H, d J1.3 Hz); 7.4–8.0 (7H, m); 8.09 (1H, broad s); 8.18 (2H, d J8.8 Hz).

EXAMPLE 24

Potassium 5R,3-(3-carbamoylphenoxy)-6S-(1R-hydroxyethyl)-7-oxo-4-thia-1-azabicyclo[3,2,0]hept-2-ene-2-carboxylate A mixture of 106 mg of 4-nitrobenzyl 5R,3-(3-carbamoylphenoxy)-6S-(1R-hydroxyethyl)-7-oxo-4-thia-1azabicyclo[3,2,0]hept-2-ene-2-carboxylate, 21.8 mg of potassium hydrogen carbonate, 150 mg of 10% palladium on charcoal, 5 ml of dioxan and 5 ml of water was hydrogenated at 420 kPa (60 psi) for 60 minutes, was filitered through diatomaceous earth and lyophilised. The yellow solid was dissolved in water, washed with ethyl acetate and lyophilised to afford 40 mg of the title compound.
$^1$H NMR (D$_2$O) δ 1.28 (3H, d J6.6 Hz); 3.92 (1H, dd J1.5 and 6.2 Hz); 4.23 (1H, m); 5.68 (1H, d J1.5 Hz); 7.39–7.20 (4H, m).

EXAMPLE 25

Potassium 5R,6S-(1R-hydroxyethyl)-3-(3-methylcarbamoylphenoxy)-7-oxo-4-thia-1-azabicyclo[3,2,0]hept-2-ene-2-carboxylate A mixture of 142 mg of 4-nitrobenzyl 5R,6S-(1R-hydroxyethyl)-3-(3-methylcarbamoylphenoxy)-7-oxo-4-thia-1-azabicyclo[3,2,0]hept-2-ene-2-carboxylate, 28 mg of potassium hydrogen carbonate, 150 mg of 10% palladium on ccharcoal, 5 ml of dioxan and 5 ml of water was hydrogenated at 345kPa (50 psi) for 60 minutes, was filtered through diatomaceous earth and lyophilised to afford 76 mg of the title compound.
$^1$H NMR (D$_2$O) δ 1.30 (3H, d J6.4 Hz); 2.92 (3H, s); 3.94 (1H, dd J 1 and 6.1 Hz); 4.25 (1H, m); 5.69 (1H, d J1 Hz); 7.0–7.7 (4H, m).

EXAMPLE 26

Pentafluorophenyl 4-acetoxybenzoate

A solution of 10.8 g of 4-acetoxybenzoyl chloride in dry acetonitrile was treated with 10 g of pentafluorophenol, and stirred at 0° C. whilst 4.4 ml of pyridine was added dropwise. The solution was permitted to warm to room temperature then heated to reflux temperature until the reaction was complete. Solvent was evaporated in vacuo and the residue obtained partitioned between ethyl acetate and water. The organic solution was washed with further portions of water and brine and dried over magnesium sulphate. Evaporation afforded 18 g of the title compound.
$v_{max}$ (film) 1760 cm$^{-1}$
$^1$H NMR (CDCl$_3$) δ 2.25 (3H, s) 7.21,8.21 (4H, AA'BB', J=9 Hz).

EXAMPLE 27

Pentafluorophenyl 4-hydroxybenzoate

Pentafluorophenyl 4-acetoxybenzoate (10 g) in tetrahydrofuran was treated with 50 ml of 5M hydrochloric acid and 150 ml of tetrahydrofuran and stirred at room temperature overnight. The solvents were evaporated in vacuo to give a product which was purified by column chromatography (silica; ethyl acetate/hexane mixtures as eluant) to afford the title compound (8 g).
$v_{max}$ (film) 1760 cm$^{-1}$
$^1$H NMR (CDCl$_3$) δ 6.86,7.01 (4H, AA'BB', J=9 Hz); 7.30 (1H, broad s).

EXAMPLE 28

Pentafluorophenyl 4-chlorothiocarbonyloxybenzoate

A solution of 1.34 g of sodium hydroxide in water was added dropwise over 15 minutes with vigorous stirring to a solution of 8.45 g of pentafluorophenyl 4-hydroxybenzoate and 3.2 ml of thiophosgene in 100 ml of chloroform at −20° C. The mixture was stirred at 5° C. until the reaction was complete and the organic layer separated, dried over calcium chloride and the solvent evaporated. Chromatography of the residue on silica gel eluting with hexane/ethyl acetate mixtures afforded 5.9 g of the title compound.
$v_{max}$ (film) 1760 cm$^{-1}$
$^1$H NMR (CDCl$_3$) δ 7.32,8.30 (4H, AA'BB', J=8 Hz)

EXAMPLE 29

4-Nitrobenzyl-2-[3(S)-1(R)-dimethyl-(2-methylprop-2-yl)-silyloxyethyl)-4(R)-ethylthioazetidin-2-on-1-yl]-3-[4-(pentafluorophenoxycarbonyl)phenoxy]-3-trimethylacetylthiopropenoate To a stirred solution of 4-nitrobenzyl 2-[3(S)-(1(R)-dimethyl-(2-methylprop-2-yl)-silyloxyethyl)-4(R)-ethylthioazetidin-2-on-1-yl]acetate (6.76 g) and pentafluorophenyl 4-chlorothiocarbonyloxybenzoate (5.89 g) in dry tetrahydrofuran at −40° C. under argon was added a solution of a mixture of 6.65 ml of hexamethyldisilazane and 19.7 ml of a 1.6 molar hexane solution of n-butyllithium in dry tetrahydrofuran. The mixture was stirred at −40° C. for 20 minutes and 3.72 ml of pivaloyl bromide was added. After stirring at −40° C. for a further hour, the mixture was poured into cold 0.1 molar aqueous hydrochloric acid and extracted with ether. The combined organic layers were washed with saturated sodium bicarbonate, with brine, and were then dried over magnesium sulphate and evaporated to dryness. Chromatography over silica gel, eluting with hexane/ethyl acetate mixtures afforded the title compound (10.9 g).
$v_{max}$ (film) 1760 cm$^{-1}$
$^1$H NMR (CDCl$_3$) δ 0.02 6H, s); 0.81,0.89 9H, 2s); 1.09,1.16 (9H, 2s); 1.16–1.32 (6H, m); 2.51–2.79 (2H, m); 3.24–3.32 (1H, m); 4.22–4.29 (1H, m); 5.25–5.47 (3H, m ; 6.95–8.24 (8H, m).

EXAMPLE 30

4-Nitrobenzyl-2-[4(R)-ethylthio-3(S)-[1(R)-hydroxyethyl]-azetidin-2-on-1-yl]-3-[4-(pentafluorophenoxycarbonyl)phenoxy]-3-trimethylacetylthiopropenoate To a stirred solution of 10.9 g of 4-nitrobenzyl 2-[3(S)-(1(R)-dimethyl-(2-methylprop-2-yl)-silyloxyethyl)-4(R)-ethylthioazetidin-2-on-1-yl]-3-[4-(pentafluorophenyl-carbonyl)-phenoxy]-3-trimethylacetylthiopropenoate in 218 ml of tetrahydrofuran at room temperature was added 43 ml of 5M hydrochloric acid. The mixture was stirred until t.l.c. showed the reaction to be complete. The mixture was partitioned between ethyl acetate and water, the separated organic layer washed with sodium bicarbonate solution and brine and dried over magnesium sulphate. Evaporation of the filtered solution followed by chromatography of the residue (silica gel, ethyl acetate/hexane mixtures as eluant) afforded the title compound (3.7 g).

The product is isolated as a mixture of E and Z isomers, observed as double peaks in the nmr spectrum. The E and Z isomers are separable by chromatography if required.

$v_{max}$ (film) 1760 cm$^{-1}$ $^1$H NMR (CDCl$_3$) δ 1.09 (9H, s); 1.16–1.34 (6H, m); 1.75 (1H, broad s); 2.69–2.76 (2H, m); 3.26 (1H, dd, J=2.5 Hz and 4.8 Hz); 4.2–4.3 (1H, m); 5.26 (1H, d, J=2.5 Hz); 5.26,5.34 (2H, ABq, J=9 Hz); 7.18,8.17 (4H, AA′BB′, J=8.8 Hz); 7.60,8.24 (4H, AA′BB′, J=8.8 Hz). Signals due to the minor propenoate isomer were also detectable.

EXAMPLE 31

4-Nitrobenzyl-2-[4()-chloro-3(S)-[1(R)-hydroxyethyl]-azetidin-2-on-1-yl]-3-[4-(pentafluorophenoxycarbonyl)-phenoxy]-3-trimethylacetylthiopropenoate To a stirred solution of 3.73 g of 4-nitrobenzyl 2-[4(R)-ethylthio-3(S)-(1(R)-hydroxyethyl)-azetidin-2-on-1-yl]-3-[4-(pentafluorophenoxycarbonyl)phenoxy]- 3-trimethylacetylthiopropenoate in 25 ml of dry chloroform at −40° C. was added a solution of 5.6 mmol chlorine in 7.2 ml of carbon tetrachloride, and the solution was stirred for 30 minutes. The reaction mixture was allowed to reach room temperature and evaporated to dryness. Chromatography of the residue (silica gel, hexane/ethyl acetate mixtures as eluant) gave the title compound (2.5 g).

$^1$H NMR (CDCl$_3$) δ 1.10 (9H, s); 1.39 (3H, d, J=6.3 Hz); 1.61 (1H, broad s); 3.54 (1H, dd, J=4.3 Hz and 9.4 Hz); 4.29–4.35 (1H, m); 5.33 (2H, s); 6.13 (1H, d J=4.3 Hz); 7.17,8.19 (4H, AA′BB′, J=8.8 Hz); 7.56,8.25 (4H, AA′BB′, J=8.8 Hz).

EXAMPLE 32

4-Nitrobenzyl 5(R),6(S)-[1(R)-hydroxyethyl]-7-oxo-3[4-(pentafluorophenoxycarbonyl)phenoxy]-4-thia-1-azabicyclo[3.2.0-]hept-2-ene-2-carboxylate 243 mg of imidazole was added to a stirred solution of 3.73 g of 4-nitrobenzyl 2-[4(S)-chloro-3(S)-(1(R)-hydroxyethyl)-azetidin-2-on-1-yl]-3-[4-(pentafluorophenoxycarbonyl)-phenoxy]-3-trimethylacetylthiopropenoate in 22 ml of dioxan-water (9:1 v/v) at 5° C. Stirring was continued for 30 minutes and the mixture was then allowed to reach room temperature and was partitioned between ethyl acetate and water. The organic layer was washed with cold dilute hydrochloric acid, saturated sodium bicarbonate and brine, dried over magnesium sulphate and evaporated in vacuo to dryness. Chromatography of the residue over silica gel and elutnng with hexane/ethyl acetate mixtures afforded the title compound (2.56 g).

$v_{max}$ (KBr) 1770 cm$^{-1}$ $^1$H NMR (CDCl$_3$) 1.39 (3H, d, J=6.3 Hz); 1.75 (1H, broad); 3.85 (1H, dd, J=1.4 Hz and 6.5 Hz); 4.28–4.33 (1H, m); 5.21,5.40 (2H, ABq, J=14.7 Hz); 5.74 (1H, d, J=1 4 Hz); 7.27,8.18 (4H, AA′BB′ J=8.9 Hz); 7.62,8.22 (4H, AA′BB′, J=8.7 Hz).

EXAMPLE 33

4-Nitrobenzyl 5R,3-(4-carbamoylphenoxy)-6S-(1R-hydroxyethyl)-7-oxo-4-thia-1-azabicyclo[3,2,0]hept-2-ene-2-carboxylate To a solution of 1.00 g of 4-nitrobenzyl 5R,6S-(1R-hydroxyethyl)-7-oxo-3-[4-(pentafluorophenoxycarbonyl)phenoxy]-4-thia-1-azabicyclo[3,2,0]hept-2-ene-2-carboxylate in 15 ml of acetonitrile at 0° C. was added a solution of 75 mg of ammonia dissolved in 5 ml of dry ethanol. The mixture was stirred at 0° C. for 15 minutes, and at room temperature for 1 hour. The precipitate was filtered off from the mixture, washed with ethyl acetate and dried in vacuo to afford 413 mg of the title compound with physical properties identical to those given in Example 10.

EXAMPLE 34

Acetoxyethyl 5R,3-(4-carbamoylphenoxy)-6S-(1R-hydroxyethyl)-7-oxo-4-thia-1-azabicyclo[3,2,0]hept-2-ene-2-carboxylate To a solution of 100 mg of potassium 5R,3(4-carbamoylphenoxy)-6S-(1R-hydroxyethyl)-7-oxo-4-thia1-azabicyclo[3,2,0]hept-2-ene-2-carboxylate in 1 ml of dry dimethylacetamide at 0° C. was added a solution of 85 μl of 1-chloroethyl acetate and 77 mg of sodium iodide in 1 ml of dry dimethylacetamide. The mixture was stirred for 18 hours and then partitioned between ethyl acetate and water. The organic layer was washed with water, was dried over anhydrous magnesium sulphate, and was evaporated to dryness. Chromatography of the residue over silica gel and elution with hexane/ethyl acetate/acetonitrile mixtures afforded 17 mg of the title compound.

$^1$H NMR (CDCl$_3$)δ 1.35and 1.37 (3H, 2d, J=6 Hz); 1.45 and 1.46 (3H, 2d, J=6.5 Hz); 3.76 (1H, dd J=1.2 and 5.8 Hz); 4.13 (1H, m); 5.66 (1H, d, J=1.2 Hz); 5.7 (1H, broad s); 6.1 (1H, broad s); 6.92 (1H, m); 7.19 and 7.20 (2H, 2d, J=8.8 Hz); 7.84 (2H, d, J=8.8 Hz).

EXAMPLE 35

(5-Methyl-2-oxo-1,3-dioxolen-4-yl)methyl 5R,3-(4-carbamoylphenoxy)-6S-(1R-hydroxyethyl)-7-oxo-4-thia-1-azabicyclo[3,2,0]hept-2-ene-2-carboxylate To a solution of 100 mg of potassium 5R,3-(4-carbamoylphenoxy)-6S-(1R-hydroxyethyl)-7-oxo-4-thia1-azabicyclo[3,2,0]hept-2-ene-2-carboxylate in 1 ml of dimethylacetamide at 0° C. was added a solution of 55 mg of 4-bromomethyl-5-methyl-1,3-dioxolen-2-one in 0.5 ml of dimethylacetamide. The mixture was stirred for 18 hours and then partitioned between ethyl acetate and water. The organic layer was washed with water, was dried over anhydrous magnesium sulphate, and was evaporated to dryness. Chromatography of the residue over silica gel and elution with hexane/ethyl acetate/acetonitrile mixtures afforded 39 mg of the title compound $^1$H NMR (CD$_3$CN)δ1.23 (3H, d, J=6.3 Hz); 2.07 (3H, s); 3.84 (1H, dd J=1.5 and 5.5 Hz); 4.14 (1H, m); 4.8 and 4.95 22H, AB, J=14.1 Hz); 5.71 (1H, d, J=1.5 Hz); 6.1 (1H, broad s) 6.8 (1H, broad s); 7.24 and 7.85 (4H, AA′BB′, J=8.8 Hz)

EXAMPLE 36

Ethoxycarbonyloxymethyl 5R,3-(4-carbamoylphenoxy)-6S-(1R-hydroxyethyl)-7-oxo-4-thia-1-azabicyclo[3,2,0]-hept-2-ene-2-carboxylate To a solution of 100 mg of potassium 5R,3-(4-carbamoylphenoxy)-6S-(1R-hydroxyethyl)-7-oxo-4-thia1-azabicyclo[3,2,0]hept-2-ene-2-carboxylate in 1 ml of dry dimethylformamide at 0° C. was added a solution of 85 μl of ethyl-iodomethyl-carbonate in 0.5 ml of dry dimethylformamide. The mixture was stirred for 3 hours and then partitioned between ethyl acetate and water. The organic layer was washed with water, was dried over anhydrous magnesium sulphate, and was evaporated to dryness. Chromatography of the residue over silica gel and elution with hexane/ethyl acetate/acetonitrile mixtures afforded 63 mg of the title compound.

$^1$H NMR (CD$_3$CN)δ 1.22 (3H, d J=7 Hz); 1.24 (3H, t J=7 Hz); 3.83 (1H, dd J=1.5 and 5.5 Hz); 4.13 (1H, m); 5.70 (1H, d J=1.5 Hz); 5.72 and 5.79 (2H, AB J=6 Hz); 6.1 (1H, broad s); 6.9 (1H, broad s); 7.28 and 7.88 (4H, AA'BB' J=8.8 Hz

EXAMPLE 37

Acetoxymethyl 5R,3-(4-carbamoylphenoxy)-6S-(1R-hydroxyethyl)-7-oxo-4-thia-1-azabicyclo[3,2,0]hept-2-ene-2-carboxylate To a solution of 180 mg of potassium 5R,3-(4-carbamoylphenoxy)-6S-(1R-hydroxyethyl)-7-oxo-4-thia-1-azabicyclo[3,2,0]hept-2-ene-2-carboxylate in 1 ml of dry dimethylformamide at 0° C. was added a solution of 190 mg of iodomethyl acetate in 1 ml of dry dimethylformamide. The mixture was stirred for 3 hours and then partitioned between ethyl acetate and water. The organic layer was washed with water, was dried over anhydrous magnesium sulphate, and was evaporated to dryness. Chromatography of the residue over silica gel and elution with hexane/ethyl acetate/acetonitrile mixtures afforded 56 mg of the title compound.

$^1$H NMR (CD$_3$CN)δ 1.22 (3H, d J=6.3 Hz); 2.01 (3H, s); 3.83 (1H, dd J=1.5 and 5.5 Hz); 4.13 (1H, m); 5.70 (1H, d J=1.5 Hz); 5.71 and 5.77 (2H, AB J=6 Hz); 6.1 (1H, broad s); 6.9 (1H, broad s); 7.27 and 7.88 (4H, AA'BB' J=8.8 Hz)

EXAMPLE 38

4-Nitrobenzyl 5R,6S-(1R-acetoxyethyl)-3-(4-carbamoylphenoxy)7-oxo-4-thia-1-azabicyclo[3,2,0]hept-2-ene-2-carboxylate To a suspension of 200 mg of 4-nitrobenzyl 5R,3-(4-carbamoylphenoxy)-6S-(1R-hydroxyethyl)-7-oxo-4-thia-1-azabicyclo[3,2,0]hept-2-ene-2-carboxylate in 5 ml of dry tetrahydrofuran at 20° C. was added 5 mg of 4-dimethylaminopyridine and 389 μl of acetic anhydride. The mixture was stirred for 15 minutes and then partitioned between ethyl acetate and water. The organic layer was washed with aqueous sodium bicarbonate solution, with water, with brine, was dried over anhydrous magnesium sulphate, and was evaporated to dryness. Chromatography of the residue over silica gel and elution with hexane/ethyl acetate/acetonitrile mixtures afforded 157 mg of the title compound.

$\nu_{max}$ (CDCl$_3$) 1793 cm$^{-1}$ $^1$H NMR (CDCl$_3$) δ 1.42 (3H, d J=6.4 Hz); 2.05 (3H, s); 3.91 (1H, dd J=1.5 and 7.6 Hz); 5.2 (1H, m); 5.23 and 5.39 (2H, AB J=13.7 Hz); 5.64 (1H, d J=1.5 Hz); 5.9 (2H, broad s); 7.19 and 7.83 (4H, AA'BB' J=8.8 Hz); 7.52 and 8.18 (4H, AA'BB' J=8.8 Hz).

EXAMPLE 39

Potassium 5R,6S-(1R-acetoxyethyl)-3-(4-carbamoylphenoxy)-7-oxo-4-thia-1-azabicyclo[3,2,0]hept-2-ene-2-carboxylate A mixture of 150 mg of 4-nitrobenzyl 5R,6S-(1R-acetoxyethyl)-3-(4-carbamoylphenoxy)-7-oxo-4-thia-1azabicyclo[3,2,0]hept-2-ene-2-carboxylate, 5 ml of dioxane, 5 ml of water, 150 mg of 10% palladium on charcoal, and 28.5 mg of potassium bicarbonate was hydrogenolysed under 3 atmospheres of hydrogen for 60 minutes at room temperature, and was then filtered through diatomaceous earth. Lyophilisation of the filtrate afforded a yellow solid, which was dissolved in water and extracted with ethyl acetate. Lyophilisation of the aqueous layer afforded 99 mg of the title compound.

$^1$H NMR (D$_2$O) δ 1.38 (3H, d J=6.4 Hz); 2.14 (3H, s); 4.21 (1H, dd J=1.4 and 5.4 Hz); 5.3 (1H, m); 5.82 (1H, d J=1.4 Hz); 7.34 and 7.88 (4H, AA'BB' J=9 Hz).

EXAMPLE 40

S-Phenyl 4-(acetoxy)thiobenzoate

Copper (I) thiophenoxide (4.06 g) was added to a solution of 4-acetoxybenzoyl chloride (4.67 g) in dry acetonitrile (40 ml). The mixture was heated to reflux for 2 hours, cooled, and the solvent evaporated in vacuo. The residue was taken up in ethyl acetate, and the filtered solution washed successively with a cold, dilute ammonia solution, water and brine. Evaporation of the solution, which had been dried over magnesium sulphate, afforded the desired thioester (5.53 g).

$^1$H NMR (CDCl$_3$) δ 2.30 (3H, s); 7.00–7.60 (5H, m); 7.14, 7.98 (4H, AA'BB', J=9 Hz).

EXAMPLE 41

S-Pheny 4-(hydroxy)thiobenzoate

S-Phenyl 4-(acetoxy)thiobenzoate (5.53 g) in tetrahydrofuran was treated with 25 ml of 5.6M hydrochloric acid and stirred at room temperature overnight. The solvents were evaporated in vacuo to give a product which was purified by column chromatography (silica; ethyl acetate/hexane mixtures as eluant) to afford the title compound (4.08 g).

$^1$H NMR (d$^6$-DMSO) δ 7.58 (5H, broad s); 7.06, 8.03 (4H, AA'BB', J=9 Hz)

EXAMPLE 42

S-Phenyl 4-(chlorothiocarbonyloxy)thiobenzoate

A solution of sodium hydroxide (1.55 g) in 150 ml of water was added dropwise with vigorous stirring to a solution of 8.8 g of S-phenyl 4-(hydroxy)thiobenzoate and 3.70 ml of thiophosgene in 250 ml of chloroform, the temperature being kept below 10° C. The mixture was stirred at room temperature for 2 hours and the organic layer separated. The organic layer was washed successively with water and brine, dried over calcium chloride, and evaporated to dryness in vacuo to give 11.57 g of the title compound.

$\nu_{max}$ (film) 1665 cm$^{-1}$ $^1$H NMR (CDCl$_3$) δ 7.28, 8.14 (4H, AA'BB', J=9 Hz); 7.40–7.58 (5H, m)

EXAMPLE 43

4-Nitrobenzyl 2-[3(S)-(1(R)-dimethyl-(2-methylprop-2-yl)-silyloxyethyl)-4(R)-ethylthioazetidin-2-on-1-yl]-3-[4-(phenylthio-(carbonyl))-phenoxy]-3-trimethylacetylthiopropenoate To a stirred solution of 4-nitrobenzyl 2-[3(S)-(1(R)-dimethyl-(2-methylprop-2-yl)-silyloxyethyl)-4(R)-ethylthioazetidin-2-on-1-yl]acetate (3.91 g) and S-phenyl 4-(chlorothiocarbonyloxy)thiobenzoate (5 g) in dry tetrahydrofuran at −40° C. under argon was added a solution of a mixture of 5.1 ml of hexamethyldisilazane and 15.2 ml of a 1.6 molar hexane solution of n-butyllithium in dry tetrahydrofuran. The mixture was stirred at −40° C. for 20 minutes and 3.06 ml of trimethylacetyl bromide added. After stirring at −40° C. for a further hour, the mixture was poured into cold 0.1 molar aqueous hydrochloric acid and extracted with ether. The combined organic layers were washed with saturated sodium bicarbonate, with brine, and were then dried over magnesium sulphate and evaporated to dryness. Chromatography over silica gel, eluting with hexane/ethyl acetate mixtures afforded the title compound (5.02 g).

$^1$H NMR (CDCl$_3$) δ 0.01, 0.02 (6H, 2s); 0.77, 0.83 (9H, 2s); 1.03, 1.11 (9H, 2s); 1.15–1.50 (6H, m); 2.50–2.85 (2H, m); 3.15–3.55 (1H, m); 4.15–4.25 (1H, m); 5.20–5.45 (3H, m); 6.85–7.60 (9H, m); 7.90–8.25 (4H, m).

EXAMPLE 44

4-Nitrobenzyl 2-[4(R)-ethylthio-3(S)-(1(R)-hydroxyethyl)azetidin-2-on-1-yl]-3-[4-(phenylthio-(carbonyl))-phenoxy]-3-trimethylacetylthiopropenoate To a stirred solution of 5.04 g of 4-nitrobenzyl 2-[3(S)-(1(R)-dimethyl-(2-methylprop-2-yl)-silyloxyethyl)-4(R)-ethylthioazetidin-2-on-1-yl]-3-[4-(phenylthio(carbonyl))-phenoxy]-3-trimethylacetylthiopropenoate in 80 ml of tetrahydrofuran at room temperature was added 5 ml of water and 5 ml of concentrated hydrochloric acid. The mixture was stirred until t.l.c. showed the reaction to be complete. The mixture was partitioned between ethyl acetate and water, the separated organic layer washed with sodium bicarbonate solution and brine and dried over magnesium sulphate. Evaporation of the filtered solution followed by chromatography of the residue (silica gel, ethyl acetate/hexane mixtures as eluant) afforded the title compound((2.75 g).

The product is isolated as a mixture of E and Z isomers, observed as double peaks in the nmr spectrum. The E and Z isomers are separable by chromatography if required.

$^1$H NMR (CDCl$_3$) δ 1.12,1.19 (9H, s); 1.25–1.45 (6H, m); 1.68,1.80 (1H, 2d, broad s); 2.67–2.90 (2H, m); 3.27–3.33 (1H, m); 4.22–4.50 (1H, m); 5.25–5.47 (3H, m); 7.08–7.68 (9H, m); 7.99–8.35 (4H, m). Small signals due to the minor propenoate isomer were also detectable.

EXAMPLE 45

4-Nitrobenzyl 2-[4(S)-chloro-3(S)-(1(R)-hydroxyethyl)azetidin-2-on-1-yl]-3-[4-(phenylthio-(carbonyl))phenoxy]-3-trimethylacetylthiopropenoate To a stirred solution of 2.75 g of 4-nitrobenzyl 2-[4(R)-ethylthio-3(S)-(1(R)-hydroxyethyl)-azetidin-2-on-1-yl]-3-[4-(phenylthio-(carbonyl))-phenoxy]-3-trimethylacetylthiopropenoate in 25 ml of dry chloroform at −40° C. was added a solution of 5.3 mmol of chlorine in 7 ml of carbon tetrachloride, and the solution was stirred for 30 minutes. The reaction mixture was allowed to reach room temperature and evaporated to dryness. Chromatography of the residue (silica gel, hexane/ethyl acetate mixtures as eluant) gave the title compound (1.98 g)

$^1$H NMR (CDCl$_3$) δ 1.09 (9H, s); 1.41 (3H, d, J=6.3 Hz); 2.30 (1H, broad s); 3.54 (1H, dd, J=4.3 Hz and 9.6 Hz); 4.27–4.40 (1H, m); 5.34 (2H, apparent s); 6.16 (1H, d, J=4.3 Hz); 7.08–7.63 (9H, m); 7.98–8.28 (4H, m)

EXAMPLE 46

4-Nitrobenzyl 5(R),6(S)-[1(R)-hydroxyethyl]-7-oxo-3[4-(phenylthio-(carbonyl))phenoxy]-4-thia-1-azabicyclo[3.2.0]hept-2-ene-2-carboxylate 0.542 g of imidazole was added to a stirred solution of 5.06 g of 4-nitrobenzyl 2-[4(S)-chloro-3(S)-(1(R)-hydroxyethyl)-azetidin-2-on-1-yl]-3-[4-(phenylthio-(carbonyl))phenoxy]-3-trimethylacetylthiopropenoate in dioxan-water (9:1 v/v) at 5° C. Stirring was continued for 30 minutes and the mixture was then allowed to reach room temperature and was partitioned between ethyl acetate and water. The organic layer was washed with cold dilute hydrochloric acid, saturated sodium bicarbonate and brine, dried over magnesium sulphate and evaporated in vacuo to dryness. Chromatography of the residue over silica gel and eluting with hexane/ethyl acetate mixtures afforded the title compound (3.24 g).

$\nu_{max}$ (CDCl$_3$) 1786 cm$^{-1}$ $^1$H NMR (CDCl$_3$) δ 1.39 (3H, d, J=6.3 Hz); 1.80 (1H, broad s); 3.83 (1H, dd, J=1.1 Hz and 6.7 Hz); 4.23–4.44 (1H, m); 5.22,5.41 (2H, ABq, J=13.7 Hz); 5.71 (1H, d, J=1.1 Hz); 7.22,8.05 (4H, AA'BB', J=8.8 Hz); 7.52,8.19 (4H, AA'BB', J=8.7 Hz); 7.40–7.54 (5H, m).

EXAMPLE 47

4-Nitrobenzyl 5(R),6(S)-[1(R)-hydroxyethyl]-7-oxo-3-[4-(N-propylcarbamoyl)phenoxy]-4-thia-1-azabicyclo[3.2.0]hept-2-ene-2-carboxylate 14.5 μl of n-propylamine in dry acetonitrile was added dropwise over 10 minutes to a cool (0° C.), stirred solution of 51 mg of 4-nitrobenzyl 5(R),6(S)-[1(R)-hydroxyethyl]-7-oxo-3-[4-(phenylthio-carbonyl)-phenoxy]-4-thia-1-azabicyclo[3.2.0]hept-2-ene-2-carboxylate and 34 mg of silver trifluoromethanesulphonate in dry acetonitrile. The mixture was stirred at room temperature protected from light until the reaction was complete. The solution was filtered and the filtrate evaporated in vacuo and the residue chromatographed on silica gel using hexane/ethyl acetate mixtures as eluant to give 23 mg of the title compound.

$\nu_{max}$ (CDCl$_3$) 1784 cm$^{-1}$ $^1$H NMR CDCl$_3$) δ 1.00 (3H, t, J=7.3 Hz); 1.38 (3H, d, J=6.3 Hz); 1.57–1.76 (2H, m); 3.37–3.49 (2H, m); 3.79 (1H, dd, J=1.4 Hz and 6.8 Hz); 4.25–4.37 (1H, m); 5.23,5.43 (2H, ABq, J=13.8 Hz); 5.67 (1H, d, J=1.4 Hz); 6.15 (1H, t, J=8.8 Hz); 7.18,7.78 (4H, AA'BB', J=8.8 Hz); 7.54,8.81 (4H, AA'BB', J=8.8 Hz).

EXAMPLE 48

4-Nitrobenzyl 5(R),6(S)-[1(R)-hydroxyethyl]-3[4-(N-methylcarbamoyl)phenoxy]-7-oxo-4-thia-1azabicyclo[3.2.0]hept-2-ene-2-carboxylate 44 mg of the above compound were obtained from 87.5 mg of 4-nitrobenzyl 5(R),6(S)-[1(R)-hydroxyethyl]-3[4-(phenylthio-carbonyl)phenoxy]-7-oxo-4-thia-1-azabicyclo[3.2.0]hept-2-ene-2-carboxylate by a procedure analogous to that described in Example 47, using 58 mg of silver trifluoromethanesulphonate and 0.45 mmol of methylamine (as an ethereal solution).

$\nu_{max}$ (CHCl$_3$) 1780 cm$^{-1}$ $^1$H NMR (d$^6$-acetone) δ 1.19 (3H, d, J=6.4 Hz); 2.86 (3H, s); 3.80 (1H, dd, J=1.5 Hz and 6.3 Hz); 4.06–4.17

(1H, m); 5.17,5.34 (2H, ABq, J=14.2 Hz); 5.74 (1H, d, J=1.5 Hz); 7.22,7.85 (4H, AA'BB', J=8.8 Hz); 7.55,8.08 (4H, AA'BB', J=8.8 Hz); 7.71 (1H, broad s)

We claim:

1. A compound of formula I

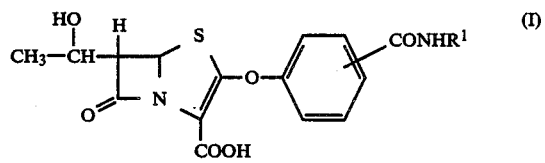

and esters thereof at the 2-carboxylic acid group and/or at the 8-hydroxy group, and physiologically tolerable salts thereof, in which $R^1$ represents a hydrogen atom or an alkyl group having from 1 to 4 carbon atoms, the $CONHR^1$ group being present on the 3- or 4-position of the phenyl ring.

2. A compound according to claim 1 which is 3-(4-Carbamoylphenoxy)-6-(1-hydroxyethyl)-7-oxo-4-thia-1-azabicyclo[3,2,0]hept-2-ene-2-carboxylic acid.

3. A compound according to claim 1 which is 3-(3-Carbamoylphenoxy)-6-(1-hydroxyethyl)-7-oxo-4-thia-1-azabicyclo[3,2,0]hept-2-ene-2-carboxylic acid.

4. A compound according to claim 1 which is 5R,3-(4-Carbamoylphenoxy)-6S-(1R-hydroxyethyl)-7-oxo-4-thia-1-azabicyclo[3,2,0]hept-2-ene-2-carboxylic acid.

5. A compound according to claim 1 which is 5R,3-(3-Carbamoylphenoxy)-6S-(1R-hydroxyethyl)-7-oxo-4-thia-1-azabicyclo[3,2,0]hept-2-ene-2-carboxylic acid.

6. An ester at the 2-carboxy group of a compound of formula I as claimed in claim 1.

7. An ester as claimed in claim 6, which can be converted by hydrolysis, by photolysis, by reduction or by esterase enzyme action, to give a free acid of formula I as claimed in claim 1.

8. An ester as claimed in claim 6, which has been formed between a free acid as claimed in claim 1 and an aliphatic alcohol or phenol having up to 20 carbon atoms in total.

9. An ester as claimed in claim 6, wherein the esterified carboxy group at position 2 is a —$COOR^2$ group, in which $R^2$ represents a methyl or ethyl group which is substituted by an acyloxy group, by an aminoalkanoyloxy group, or when $R^2$ is an ethyl group by an optionally substituted 2-amino group, or by one or more unsubstituted or substituted phenyl groups.

10. An ester as claimed in claim 9, wherein a phenyl group is substituted by one or more substituents selected from nitro groups and halogen atoms.

11. An ester as claimed in claim 10, wherein $R^2$ is a benzyl, p-nitrobenzyl, benzhydryl or trityl group.

12. An ester as claimed in claim 7, wherein the ester group is removable by esterase enzyme action under physiological conditions to give the free acid or a carboxylate salt.

13. An ester as claimed in claim 12, which is an acyloxymethyl or 1'-(acyloxy)ethyl ester, a 5-methyldioxalen-2-on-4-yl-methyl ester, an aminoalkanoyloxymethyl ester, a phthalidyl ester, a 1'-(alkoxycarbonyloxy)ethyl ester, or an optionally substituted 2-aminoethyl ester, or an alkoxycarbonyloxymethylester.

14. An ester as claimed in claim 13, being a glycyloxymethyl, L-valyloxymethyl, L-leucyloxymethyl, 1'-(methoxycarbonyloxy)ethyl, 2-diethylaminoethyl or 2-(1-morpholino)-ethyl ester.

15. A p-nitrobenzyl, phthalidyl, pivaloyloxymethyl, ethoxycarbonyloxymethyl, 5-methyldioxalen-2-on-4-yl-methyl, acetylmethyl, acetoxymethyl, 1'-(acetoxy)ethyl, 1'-(acetyl)ethyl or 1'-(ethoxycarbonyloxy)ethyl or -methylester of a compound as claimed in claim 1.

16. A salt of a compound as claimed in claim 1.

17. A physiologically tolerable salt of a compound as claimed in claim 1.

18. A salt as claimed in claim 1, which is an alkali metal or alkaline earth metal salt, an ammonium salt, or is a physiologically tolerable acid addition salt.

19. A compound, ester or salt as claimed in claim 1, wherein the 8-hydroxy group is esterified.

20. A compound a claimed in claim 19, wherein the 8-ester group is removable under physiological conditions, for example, a group $R_xCO$— in which R represents a hydrogen atom or a straight or branched chain alkyl group having from 1 to 4 carbon atoms, or represents a phenyl group or a phenoxyalkyl group in which the alkyl moiety is straight-chained or branched and has up to 4 carbon atoms.

21. An ester or salt according to claim 1 of 3-(4-Carbamoylphenoxy)-6-(1-hydroxymethyl)-7-oxo-4-thia-1-azabicyclo[3,2,0]hept-2-ene-2-carboxylic acid.

22. An ester or salt according to claim 1 of 5R,3-(4-Carbamoylphenoxy)-6S-(1R-hydroxyethyl)-7-oxo-4-thia-1-azabicyclo[3,2,0]hept-2-ene-2-carboxylic acid.

23. A compound as claimed in claim 1, having R-stereochemistry at position 5, S stereochemistry at position 6, and R stereochemistry at position 8.

24. A pharmaceutical preparation useful as an antibacterial which comprises a compound formula I, an ester thereof at the 2-carboxylic acid group and/or at the 8-hydroxy group, or a physiological tolerable salt thereof, as claimed in claim 1, in admixture or conjuction with a pharmaceutically suitable carrier.

25. A pharmaceutical preparation useful as an antibacterial as claimed in claim 24, which comprises a compound as claimed in claim 4, or an ester or salt as claimed in claim 22, in admixture or conjuction with a pharmaceutically suitable carrier.

26. The use of a compound, ester or salt as claimed in claim 1 for the manufacture of a medicament for the treatment of bacterial infections.

* * * * *

UNITED STATES PATENT AND TRADEMARK OFFICE
CERTIFICATE OF CORRECTION

PATENT NO. : 4,795,748

DATED : January 3, 1989

INVENTOR(S) : Barry C. Ross et al.

It is certified that error appears in the above-identified patent and that said Letters Patent is hereby corrected as shown below:

Claim 20, Column 36, Line 28, change "in which R..." to --in which $R_x$...--.

Signed and Sealed this

Fifteenth Day of August, 1989

Attest:

DONALD J. QUIGG

*Attesting Officer*  *Commissioner of Patents and Trademarks*